United States Patent
Xie et al.

(10) Patent No.: US 12,264,320 B2
(45) Date of Patent: Apr. 1, 2025

(54) METHODS OF IMPROVING DROUGHT AND SALT RESISTANCE IN A PLANT AND GENETICALLY ENGINEERED PLANTS WITH IMPROVED DROUGHT AND SALT RESISTANCE

(71) Applicant: UT-Battelle, LLC, Oak Ridge, TN (US)

(72) Inventors: Meng Xie, Oak Ridge, TN (US); Jin-Gui Chen, Oak Ridge, TN (US); Wellington Muchero, Oak Ridge, TN (US); Chongle Pan, Norman, OK (US); Daniel M. Close, Knoxville, TN (US); Emily B. Gee, Oak Ridge, TN (US); Qiuming Yao, Lincoln, NE (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 17/003,053

(22) Filed: Aug. 26, 2020

(65) Prior Publication Data
US 2021/0062213 A1 Mar. 4, 2021

Related U.S. Application Data

(60) Provisional application No. 62/891,537, filed on Aug. 26, 2019.

(51) Int. Cl.
*C12N 15/82* (2006.01)
(52) U.S. Cl.
CPC .............................. *C12N 15/8273* (2013.01)
(58) Field of Classification Search
None
See application file for complete search history.

(56) References Cited

U.S. PATENT DOCUMENTS

2011/0281765 A1* 11/2011 Bush .................... C12Q 1/6895
506/16
2014/0317781 A1 10/2014 Maor et al.

OTHER PUBLICATIONS

Kilian et al. "The AtGenExpress global stress expression data set: protocols, evaluation and model data analysis of UV-B light, drought and cold stress responses". Plant Journal. 50:347-83. (Year: 2007).*
Zapata et al. "Chromosome-level assembly of *Arabidopsis thaliana* Ler reveals the extent of translocation and inversion polymorphisms". Proc Natl Acad Sci USA. 113(28):E4052-60. (Year: 2016).*
Duan and Cai. "OsLEA3-2, an Abiotic Stress Induced Gene of Rice Plays a Key Role in Salt and Drought Tolerance". PLOS One. 7(9):1-11. (Year: 2012).*
Guo et al. "Protein tolerance to random amino acid change". PNAS. 101: 9205-9210. (Year: 2004).*
Tuskan et al. Science. 313(5793):1596-604. (Year: 2006).*
Takada, I. Mol Cell Biol. 35(2): 344-55. (Year: 2015).*
NCBI Reference Sequence: XP_003617969.1 (Year: 2018).*
Lin et al. "Identifying RNA splicing factors using IFT genes in Chlamydomonas reinhardtii". Open Biology. 8(3). (Year: 2018).*
Anand A. et al., "*Arabidopsis* Vire2 Interacting Protein2 is Required for Agrobacterium T-DNA Integration in Plants", The Plant Cell, vol. 19, pp. 1695-1708 (May 2007).
Forment, J. et al., "Expression of *Arabidopsis* SR-like splicing proteins confers salt tolerance to yeast and transgenic plants", The Plant Journal, vol. 30, No. 5, pp. 511-519 (2002).
Goldmuntz, E. et al., "Microdeletions of chromosomal region 22q11 in patients with congenital conotruncal cardiac defects", J Med Genet, vol. 30, pp. 807-812 (1993).
Golldack, D. et al., "Tolerance to drought and salt stress in plants: Unraveling the signaling networks.", Frontiers in Plant Science, vol. 5, article 151, pp. 1-10 (Apr. 22, 2014).
Gong, W. et al., "Structural and mutational analysis of a conserved gene (DGSI) from the minimal DiGeorge syndrome critical region", Hum Mol Genet, vol. 6, No. 2, pp. 267-276 (1997).
Isayenkov, S.V., "Physiological and molecular aspects of salt stress in plants", Cytology and Genetics, vol. 46, No. 5, pp. 302-318 (2012).
Ji, H. et al., "The Salt Overly Sensitive (SOS) Pathway: Established and Emerging Roles", Mol Plant, vol. 6, No. 2, pp. 275-286 (Mar. 2013).
Knight, H. et al., "The sfr6 Mutation in *Arabidopsis* Suppresses Low-Temperature Induction of Genes Dependent on the CRT/DRE Sequence Motif", The Plant Cell, vol. 11, 875-886 (May 1999).
Kreps, J.A. et al., "Transcriptome Changes for Arabidopsis in Response to Salt, Osmotic, and Cold Stress", Plant Physiol, vol. 130, pp. 2129-2141 (Dec. 2002).
Kurkela, S. et al., Structure and expression of kin2, one of two cold- and ABA-induced genes of *Arabidopsis thaliana*, Plant Mol Biol, vol. 19, pp. 689-692 (1992).

(Continued)

*Primary Examiner* — Matthew R Keogh
*Assistant Examiner* — David R Byrnes
(74) *Attorney, Agent, or Firm* — Scully, Scott, Murphy & Presser, P.C.

(57) ABSTRACT

The present disclosure provides methods for increasing drought resistance, salt resistance, and biomass production of a plant. The methods encompass expression of DiGeorge-Syndrome Critical Region 14 (DGCR14) gene in the plant. In comparison to a plant not manipulated in this manner, the disclosed, genetically-modified, plants display improved drought resistance and salt resistance. Also provided are plants that can be obtained by the method according to the invention, and nucleic acid vectors to be used in the described methods.

10 Claims, 10 Drawing Sheets
(8 of 10 Drawing Sheet(s) Filed in Color)
Specification includes a Sequence Listing.

(56) References Cited

OTHER PUBLICATIONS

Lindsay, E.A. et al., "Congenital heart disease in mice deficient for the DiGeorge syndrome region", Nature, vol. 401, pp. 379-383 (Sep. 23, 1999).
Maldonado-Bonilla, L.D., "Composition and function of P bodies in *Arabidopsis thaliana*", Frontiers in Plant Science, vol. 5, article 201, pp. 1-11 (May 14, 2014).
Mantyla, E. et al., "Role of Abscisic Acid in Drought-Induced Freezing Tolerance, Cold Acclimation, and Accumulation of LT178 and RAB18 Proteins in *Arabidopsis thaliana*", Plant Physiol, vol. 107, pp. 141-148 (1995).
Msanne, J. et al., "Characterization of abiotic stress-responsive *Arabidopsis thaliana* RD29A and RD29B genes and evaluation of transgenes", Planta 234, pp. 97-107 (Mar. 4, 2011).
Nakayama, K. et al., "*Arabidopsis* Cor15am is a Chloroplast Stromal Protein That Has Cryoprotective Activity and Forms Oligomers", Plant physiology, vol. 144, pp. 513-523 (May 2007).
Perea-Resa, C. et al., "The LSM1-7 Complex Differentially Regulates *Arabidopsis* Tolerance to Abiotic Stress Conditions by Promoting Selective mRNA Decapping", The Plant Cell, vol. 28, pp. 505-520 (Feb. 2016).
Rizzu, P. et al. "Cloning and comparative mapping of a gene from the commonly deleted region of DiGeorge and Velocardiofacial syndromes conserved in C. elegans", Mammalian Genome, vol. 7, pp. 639-643 (1996).
Strizhov, N. et al., "Differential expression of two P5CS genes controlling proline accumulation during salt-stress requires ABA and is regulated by ABA1, ABI1 and AXR2 in *Arabidopsis*", The Plant Journal, vol. 12, No. 3, pp. 557-569 (1997).
Takada, I., "DGCR14 Induces Il17a Gene Expression through the RORγ/BAZ1B/RSKS2 Complex", Molecular and Cellular Biology, vol. 35, No. 2, pp. 344-355 (Jan. 2015).
Takada, I. et al., "Ess2 bridges transcriptional regulators and spliceosomal complexes via distinct interacting domains", Biochem Biophys Res Commun, vol. 497, pp. 597-604 (2018).
Theobald, D.L., "A formal test of the theory of universal common ancestry", Nature, vol. 465, pp. 219-222 (May 13, 2010).
Umezawa, T. et al., "Genetics and Phosphoproteomics Reveal a Protein Phosphorylation Network in the Abscisic Acid Signaling Pathway in *Arabidopsis thaliana*", Science Signaling, vol. 6, issue 270, rs8, pp. 1-15 (Apr. 9, 2013).
Wilson, D. et al., "Minimum prevalence of chromosome 22q11 deletions", American Journal of Human Genetics, vol. 55, issue suppl.3, conference 44, Annual Meeting of the American Society of Human Genetics, abstract only, https://www.osti.gov/biblio/133955-minimum-prevalence-chromosome-deletions (Sep. 1, 1994).
Xie, M. et al., "A 5-Enolpyruvylshikimate 3-phosphate Synthase Functions as a Transcriptional Repressor in Populus", The Plant Cell, vol. 30, pp. 1645-1660 (Jul. 2018).
Taricani, L., et al., "The Fission Yeast ES2 Homologue, Bis1, Interacts with the Ish1 Stress-responsive Nuclear Envelope Protein", The Journal of Biological Chemistry, Mar. 22, 2002, pp. 10562-10572, vol. 277, No. 12.
"Invitation to Pay Additional Fees" dated Nov. 17, 2020, received in a corresponding foreign application, namely International Application No. PCT/US20/47895.
Kanno T. et al., "A Collection of Pre-mRNA Splicing Mutants in *Arabidopsis Thaliana*", Genes, Genomes, Genetics 10(6):1983-1996 (Jun. 2020).
Purcell L, "Drought? Don't Forget the Trees! Educational Pamphlet", (online), Purdue University, Department of Forestry & Natural Resources (Oct. 2013).
Salanoubat M. et al., F17a17.13. UniProtKB entry (online). UniProt Consortium (Jul. 31, 2019).
Salanoubat M. et al., *Arabidopsis thaliana* DGCR14-Like Protein (AT3G07790), mRNA. Genbank entry (online), National Center for Biotechnology Information (Feb. 14, 2019).
International Search Report & Written Opinion dated Feb. 8, 2021 received in International Application No. PCT/US20/47895.
Liu D. et al., "The Rice ERF Transcription Factor OsERF922 Negatively Regulates Resistance to Magnaporthe Oryzae and Salt Tolerance", Journal of Experimental Botany 63(10):3899-3912 (2012).
Tao Z. et al., "OsWRKY45 Alleles Play Different Roles in Abscisic Acid Signalling and Salt Stress Tolerance But Similar Roles in Drought and Cold Tolerance in Rice", Journal of Experimental Botany 62(14):4863-4874 (2011).
Zhou Q-Y et al., "Soybean WRKY-Type Transcription Factor Genes, GmWRKY13, GmWRKY21, and GmWRKY54, Confer Differential Tolerance to Abiotic Stresses in Transgenic *Arabidopsis* Plants", Plant Biotechnology Journal 6:486-503 (2008).

* cited by examiner

B

```
Has DGCR14/ESS2   M--------------------------------ETPGASASSLLLPAASRPPKREAGEAGAATSKQ
Ath DGCR14I       MFLSPGHSPRQISSPSPSSYSDDTLRSTPRSSSSEII-----PRNPRKR-----------------M
                  *                                .** .:*:..::     .* ****

Has DGCR14/ESS2   RVLDEEYIEGLQTVIQRDFFPDVEKLQAQKEYLEAEENGDLERMRQIAIKFGSALGKMS
Ath DGCR14I       RVLDEDAYVEAIEKIIERDYFPDITKLRDRLDWIQAVKTRDPIQIRDAQLKIIERRGKKA
                  ******.* :**.:*:::**:***: ** : ..:  : ::*: . :: *:*.  *:*:

Has DGCR14/ESS2   R------EPPPPYVTPATFETPEVHAGTGVVGNKPRPRG------RGLEDGEAGEEEKEPL
Ath DGCR14I       NHHVGDTEGKTQTPGSTFLRNFTPLDEFDGKTPRTPGVSGREFHGVEVDAGDGDEDIDLN
                  .      * .:.**.:**  .*  :   *..   ** *       *::* ..*:*. **::

Has DGCR14/ESS2   PSLDVFLSRYTSEDNASFQEIMEVAKERSRARHAWLYQAEEEFEKRQKD-NLELPSAEHQ
Ath DGCR14I       LSLDEFFRRYTSEDNESFSKILEKVNRKKKEKYGFLLEGEKEDGKSIEDVKRDRITDGYG
                  ***.*: **:*****:**.:*:*  :*  :.: : ::  *:*.*   :   *  :.

Has DGCR14/ESS2   AIESSQASVETWKYKAKNSLMYYPEG-----VPDEE------QLFKKPRQVVHKNTRFL--
Ath DGCR14I       TSDQPPSTLEGWKYTAKNLLMYHPADRGEAPLTEAERAVRLLGLTKEIVKGNTRFHGKTM
                  : ::  :: * **:***.***:* .      :.:*      .* ::   *:.****

Has DGCR14/ESS2   -RDPFSQALSRCQLQQAAALNAQHKQGKVGPDGKE-----------LIPQESPRVGGF
Ath DGCR14I       DSRPREDGSVEILYTPIAGSSPMHISGRDRDKSKRYDLDDLRKTPNPFYVESDKRADNGY
                   *    .  :  : ..*.. *.  :.:   .::             :.:**  . *:

Has DGCR14/ESS2   GFVATPSPAPGVNESPMMTWGEVENTPLRVEGSETPYVD---RTPGPAFKILEPGRRERL
Ath DGCR14I       SFVRTPSPAPGLDESPFITWGEIDGTPMRLDLEDTP-IDIGGSADGPHYNIPSAPPRDVR
                  .**.*******::***::****::.**:*::.*:**    ..*** : *   *.*  :

Has DGCR14/ESS2   GLKMANEAAAKNRAKKQEALRRVT------ENLASLTPKGLSPAMSPALQRLVSRTASKY
Ath DGCR14I       AHSLSRDASRKLRERSNSMFKKPLPSPHRSGSASPNVRTLSPAAQKFFRKAIAKSSST-
                   :::::::: *.*:*..:::: .        .::  .  ***:   : :::*.::*

Has DGCR14/ESS2   TDRALRASYTPSPARSTHLKTPASGLQTPTSTPA---------PGSATRTPLTQDPASITD
Ath DGCR14I       VDESLRASYRGASPRGA--------SPGAVTPKSVRSISRFGKDGTSSETRSP---------
                  .*.:*****  :* :.         *..* **.         .*:::. *

Has DGCR14/ESS2   NLLQLPARRKASDFF
Ath DGCR14I       ---------------
```

METHODS OF IMPROVING DROUGHT AND SALT RESISTANCE IN A PLANT AND GENETICALLY ENGINEERED PLANTS WITH IMPROVED DROUGHT AND SALT RESISTANCE

CROSS REFERENCE TO RELATED APPLICATION

This application claims the benefit of priority from U.S. Provisional Application No. 62/891,537, filed Aug. 26, 2019, the entire contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-00OR22725 awarded by the U.S. Department of Energy. The government has certain rights in this invention.

INCORPORATION BY REFERENCE OF SEQUENCE LISTING

The Sequence Listing in an ASCII text file, named as 38312_3988_Seqlist_ST25.txt of 58 KB, created on Aug. 18, 2020, and submitted to the United States Patent and Trademark Office via EFS-Web, is incorporated herein by reference.

BACKGROUND

Evolved from one common ancestor, plants and animals share various fundamental developmental processes (e.g. embryogenesis, stress responses, growth, etc.) and cellular processes (e.g. cell cycle, gene regulation, metabolism, etc.), which are mainly built on evolutionarily conserved molecular mechanisms and orthologous/homologous proteins. At the DNA and protein sequence levels, the advances in genome study have demonstrated that these conservations are also manifested via conserved motifs and/or domains. Therefore, the identification of conserved protein motif and sequence-function relationship is essential for understanding genetic features that underlie fundamental processes for plants and animals. However, the sequence-function relationship is complex, making it difficult to identify residues critical for protein functionality. Plant and animal orthologs generally have high sequence divergence that is resulted from millions of years of divergent evolution. Essential and functional residues and motifs were conserved during this evolution-driven natural selection, which can be identified by comparing plant and animal orthologs. However, comparative studies across plant and animal kingdoms remain rare.

Salt stress is the major abiotic stress that impacts plant growth and crop production. High salt content in soil imposes various stresses (e.g. salinity stress and osmotic stress) on plants and severely inhibits plant performance Gene expression changes govern plant responses and adaption to salt stress. To date, a large number of salt stress-responsive genes have been identified via transcriptomic studies. The regulation of gene expression in response to salt stress is complex and occurs at multiple levels. The transcriptional regulation of salt stress responses has been extensively studied in the model plant Arabidopsis, which depends on abscisic acid (ABA) signaling and transcription factors. At the posttranscriptional level, mRNA metabolism, such as mRNA decay and splicing machinery, has been demonstrated to be crucial for regulating salt stress responses. In addition, protein kinases play multiple regulatory roles in salt stress responses by regulating signal transduction, mRNA metabolism, translation, and posttranslational mechanisms.

In human, deletions within a chromosomal region 22q11.2 have a high frequency in live births (1:4000) and are associated with abnormal developments. Within 22q11.2, DiGeorge Syndrome Critical Region 14/ESS-2 splicing factor homolog (DGCR14/ESS2) gene is located in a 250 kb region, which is called minimal DiGeorge syndrome (DGS) critical region. The deletion of this 250 kb region has been demonstrated to be tightly associated with a set of developmental disorders, such as DGS, velocardiofacial syndrome (VCFS), and conotruncal anomaly face syndrome (CFAFS). DGCR14/ESS2 is thought to be involved in mammal development because the transcript of DGCR14/ESS2 and its homologous gene (ES2) was detected in human heart, brain, and skeletal muscle, as well as mouse embryo. Molecular studies using the human cell model suggest that DGCR14/ESS2 may play a role in transcriptional regulation and pre-mRNA splicing. In human Th17 cells, DGCR14 was found to physically interact with a nuclear hormone receptor RETINOID-RELATED ORPHAN NUCLEAR RECEPTOR GAMMA (RORγ) and enhance RORγ's transcriptional activation on IL17a gene. Meanwhile, DGCR14/ESS2 was also found to be a component of the spliceosomal complex and associate with U1, U4, and U6 snRNAs. Despite these molecular results, the role of DGCR14/ESS2 in mammal development remains poorly studied because the complete knockout of DGCR14/ESS2 in mammal models (e.g. mouse) is lethal. This lethality further demonstrates the biological importance of DGCR14/ESS2.

DGCR14/ESS2 has a singular ortholog in the flowering plant Arabidopsis (Arabidopsis thaliana), which is named DGCR14-like (DGCR14l). Arabidopsis DGCR14l and human DGCR14/ESS2 only have 26% identity at the amino acid level.

SUMMARY OF THE DISCLOSURE

In one aspect, the disclosure is directed to a genetically modified plant, plant cell or plant tissue, wherein an exogenous nucleic acid comprising a DiGeorge-Syndrome Critical Region 14 (DGCR14) gene, or a homolog thereof, is expressed in the plant, plant cell or plant tissue.

In some embodiments, the exogenous nucleic acid comprises a sequence with at least 90% sequence identity to a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, and SEQ ID NO: 17.

In some embodiments, the exogenous nucleic acid encodes a protein with at least 90% sequence identity to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18.

In some embodiments, the exogenous nucleic acid is stably integrated into the plant genome.

In some embodiments, the plant is a monocot or a dicot.

In some embodiments, the plant is selected from the group consisting of genera Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea, and Zoysia.

Another aspect of this disclosure is directed to a method of improving drought and salt resistance in a plant, plant cell or plant tissue comprising: expressing an exogenous nucleic acid encoding a DiGeorge-Syndrome Critical Region 14 (DGCR14) gene, or a homolog thereof, in the plant, plant cell or plant tissue;

In some embodiments, the exogenous nucleic acid comprises a sequence with at least 90% sequence homology to a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, and SEQ ID NO: 17.

In some embodiments, the exogenous nucleic acid encodes a protein with at least 90% sequence homology to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18.

In some embodiments, the exogenous nucleic acid is stably integrated into the plant genome.

In some embodiments, the plant is a monocot or a dicot.

In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1C. *Arabidopsis* and human DGCR14 orthologs have high sequence divergence. (A) Phylogenetic tree of DGCR14. Black square, animal species; black circle, plant species; black triangle, microbe species. *Arabidopsis* and human DGCR14 orthologs are highlighted by red color. (B) Protein sequence alignment DGCR14 orthologs in *Arabidopsis* (Ath DGCR14l—SEQ ID NO: 2) and human (Has DGCR14/ESS2—SEQ ID NO: 4). (*) Indicates identical amino acid, (:) indicates conserved amino acid with strongly similar properties, (.) indicates conserved amino acid with weakly similar properties. (C) Comparison of protein domains between *Arabidopsis* DGCR14l and human DGCR14/ESS2. The ES domain is indicated by a black box.

DETAILED DESCRIPTION

Definitions

Figure 1A:
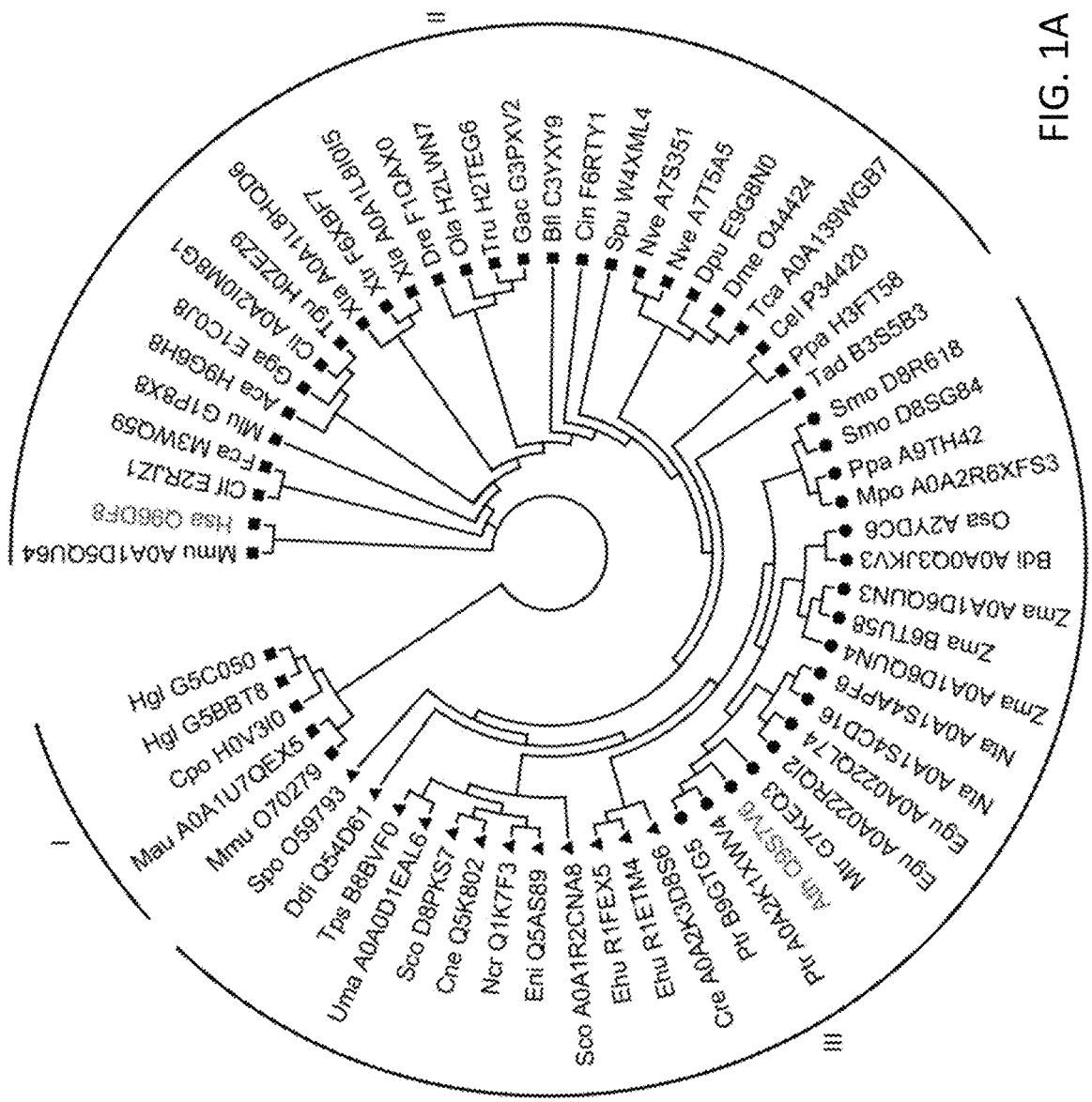

Unless defined otherwise, all technical and scientific terms used herein have the same meaning as commonly understood by one of ordinary skill in the art to which this invention belongs.

As used herein, the term "about" refers to an approximately +/−10% variation from a given value.

The term "control plant," as used herein, refers to a plant of the same species that does not comprise the modification or modifications described in this disclosure. In some embodiments, the control plant is of the same variety. In some embodiments, the control plant is of the same genetic background.

The term "DNA," as used herein, refers to a nucleic acid molecule of one or more nucleotides in length. By "nucleotide" it is meant a naturally-occurring nucleotide, as well modified versions thereof. The term "DNA" includes double-stranded DNA, single-stranded DNA, isolated DNA such as cDNA, as well as modified DNA that differs from naturally-occurring DNA by the addition, deletion, substitution and/or alteration of one or more nucleotides as described herein.

As used herein, the term "drought stress" or "drought" refers to a sub-optimal environmental condition associated with limited availability of water to a plant. Limited availability of water may occur when, for instance, rain is absent or lower and/or when the plants are watered less frequently than required. Limited water availability to a plant may also occur when for instance water is present in soil, but cannot efficiently be extracted by the plant. For instance, when soils strongly bind water or when the water has a high salt content, it may be more difficult for a plant to extract the water from the soil. Hence, many factors can contribute to result in limited availability of water, i.e. drought, to a plant. The effect of subjecting plants to "drought" or "drought stress" may be that plants do not have optimal growth and/or development. Plants subjected to drought may have wilting signs. For example, plants may be subjected to a period of at least 15 days under specific controlled conditions wherein no water is provided, e.g. without rain fall and/or watering of the plants.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase and into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG)). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states. Expression of a gene can be measured through a suitable assay, such as real-time quantitative reverse transcription polymerase chain reaction (qRT-PCR), Northern blot, transcriptome sequencing and Western blot.

The term "gene," as used herein, refers to a segment of nucleic acid that encodes an individual protein or RNA and can include both exons and introns together with associated regulatory regions such as promoters, operators, terminators, 5' untranslated regions, 3' untranslated regions, and the like.

The term "genetically modified" (or "genetically engineered" or "transgenic" or "cisgenic") refers to a plant comprising a manipulated genome or nucleic acids. In some embodiments, the manipulation is the addition of exogenous nucleic acids to the plant. In some embodiments, the manipulation is changing the endogenous genes of the plant.

The term "homologous" refers to nucleic acids or polypeptides that are highly related at the level of nucleotide or amino acid sequence. Nucleic acids or polypeptides that are homologous to each other are termed "homologues." The term "homolog" refers to a gene related to a second gene by descent from a common ancestral DNA sequence, therefore, the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%).

The term "improved drought resistance" (aka. "drought tolerance") refers to plants which, when provided with improved drought resistance, when subjected to drought or drought stress do not show effects or show alleviated effects as observed in control plants not provided with improved drought resistance. A normal plant has some level of drought resistance. It can easily be determined whether a plant has improved drought resistance by comparing a control plant with a plant provided with improved drought resistance under controlled conditions chosen such that in the control plants signs of drought can be observed after a certain period, i.e., when the plants are subjected to drought or drought stress. The plants with improved drought resistance will show less and/or reduced signs of having been subjected to drought, such as wilting, as compared to the control plants. The skilled person knows how to select suitable conditions. When a plant has "improved drought resistance," it is capable of sustaining normal growth and/or normal development when being subjected to drought or drought stress would otherwise have resulted in reduced growth and/or reduced development of normal plants. Hence, "improved drought resistance" is determined by comparing plants, whereby the plant most capable of sustaining (normal) growth under drought stress is a plant with "improved drought resistance." The skilled person is able to select appropriate conditions to determine drought resistance of a plant and how to measure signs of droughts, such as described in for example manuals by the IRRI, Breeding rice for drought prone environments, Fischer et al., 2003; and by the CIMMYT, Breeding for drought and nitrogen stress tolerance in maize: from theory to practice, Banzinger et al, 2000. Examples of methods for determining improved drought resistance in plants are provided in Snow and Tingey (1985, *Plant Physiol*, 77, 602-7) and Harb et al. (Analysis of drought stress in *Arabidopsis*, AOP 2010, *Plant Physiology Review*).

The term "improved salt resistance" or "improved salt tolerance" refers to plants which, when provided with salt resistance (or being salt resistant), when subjected to high salt stress do not show effects or show alleviated effects as observed in plants not provided with salt resistance. When a plant is "salt resistant," it is capable of sustaining normal growth and/or normal development when being subjected to a high salt environment that otherwise would have resulted in reduced growth and/or development in normal plants. Hence, salt resistance is determined by comparing plants with another plant, whereby the plant most capable of sustaining (normal) growth may be a "salt resistant" plant, whereas the plant less capable may be termed a "salt sensitive" plant. Providing salt resistance thus is understood to include improving the salt resistance of a plant, when compared with a plant not provided with salt resistance. With plants provided with salt resistance it is e.g. possible to obtain higher yields of crop and/or plant product when the plant is subjected to a period or periods of high salt conditions when compared to plants not provided with salt resistance.

As used herein, the term "nucleic acid" has its general meaning in the art and refers to refers to a coding or non-coding nucleic sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non-coding region of a genome (i.e. nuclear or mitochondrial or chloroplast).

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell*, 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

General Description

Plants

There is no specific limitation on the plants that can be used in the methods of the present disclosure, as long as the plant is suitable to be transformed by a gene. The term "plant," as used herein, includes whole plants, plant tissues or plant cells. The plants that can be used for the methods and compositions of the present disclosure include various crops, flower plants or plants of forestry, etc. Specifically, the plants include, but are not limited to, dicotyledon, monocotyledon or gymnosperm. More specifically, the plants include, but is not limited to, wheat, barley, rye, rice, corn, sorghum, beet, apple, pear, plum, peach, apricot, cherry, strawberry, *Rubus swinhoei* Hance, blackberry, bean, lentil, pea, soy, rape, mustard, opium poppy, *Olea europea, Helianthus,* coconut, plant producing castor oil, cacao, peanut, calabash, cucumber, watermelon, cotton, flax, *Cannabis,* jute, citrus, lemon, grapefruit, spinach, lettuce, asparagus, cabbage, *Brassica campestris* L. ssp. *Pekinensis, Brassica campestris* L. ssp. *chinensis,* carrot, onion, murphy, tomato, green pepper, avocado, cassia, camphor, tobacco, nut, coffee, eggplant, sugar cane, tea, pepper, grapevine, nettle grass, banana, natural rubber tree and ornamental plant, etc.

In some embodiment the methods and compositions of the present disclosure are also be used over a broad range of plant species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus, Oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus.* In some embodiments, a plant is a member of the species *Festuca arundinacea, Miscanthus* hybrid (*Miscanthus* x *giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula, alba* and *maximowiczii, Saccharum* spp., *Secale cereale, Sorghum almum, Sorghum halcapense* or *Sorghum vulgare.* In certain embodiments, the polynucleotides and vectors described herein can be used to transform a number of monocotyledonous and dicotyledonous plants and plant cell systems, wherein such plants are hybrids of different species.

In some embodiments, the plant for the methods and compositions of the present disclosure is a C3 plant. The term "C3 plant" refers to a plant that captures carbon dioxide into three-carbon compounds to enter into the Calvin cycle (photosynthesis pathway). In a C3 plant carbon dioxide capture and the Calvin cycle occur during the daytime, and stomata of C3 plants are open during the day for gas exchange, which also leads to increased water loss through the stomata (evapotranspiration). In some embodiment, the C3 plant is selected from the group consisting of genera *Allium, Arabidopsis, Brassica, Capsicum, Citrullus, Cucumis, Eucalyptus, Fragaria, Glycine, Gossypium, Hordeum,*

*Ipomoea, Malus, Manihot, Nicotiana, Oryza, Populus, Prunus, Rosa, Solanum, Spinacia* and *Triticum*.

In some embodiments, the plant for the methods and compositions of the present disclosure is a C4 plant. The term "C4 plant" refers to a plant that captures carbon dioxide into four-carbon compounds to enter into the Calvin cycle. In a C4 plant carbon dioxide capture and the Calvin cycle occur during the daytime, and stomata of C4 plants are open during the day for gas exchange, which also leads to increased water loss. In some embodiment, the C4 plant is selected from the group consisting of genera *Panicum, Saccharum, Setaria, Sorghum* and *Zea*.

Genetically Modified (Transgenic) Plants/Plant Species/Plant Cells/Plant Tissues Disclosed herein are plants and plant cells genetically modified by introduction of the disclosed exogenous nucleic acids and expression vectors to display increased salt and drought resistance/tolerance.

In some embodiments, the genetically modified plant comprises a plant that is modified to express an exogenous nucleic acid comprising a DiGeorge-Syndrome Critical Region 14 (DGCR14) gene, or a homolog thereof.

In some embodiments, the DGCR14 gene, or a homolog thereof, is from a plant. In some embodiments, the plant is *Arabidopsis*, poplar or barrelclover. In some embodiments, the DGCR14 gene, or a homolog thereof, is from an animal. In some embodiments, the DGCR14 gene is from a mammal. In some embodiments, the DGCR14 gene is selected from a mammal selected from the group consisting of a human, a mouse, a rat, a cat, a dog, a monkey, and a bat.

In some embodiments, the exogenous nucleic acid comprises a sequence with at least 90% sequence identity to a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, and SEQ ID NO: 17. In some embodiments, the exogenous nucleic acid encodes a protein with at least 90% sequence identity to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18.

TABLE 1

DNA and protein sequences of DGCR14 in different species

| Description | SEQ ID NO |
|---|---|
| *Arabidopsis thaliana* DGCR14 DNA sequence | 1 |
| *Arabidopsis thaliana* DGCR14 protein sequence | 2 |
| *Homo sapiens* (human) DGCR14 DNA sequence | 3 |
| *Homo sapiens* DGCR14 protein sequence | 4 |
| *Macaca mulatta* (monkey) DGCR14 DNA sequence | 5 |
| *Macaca mulatta* DGCR14 protein sequence | 6 |
| *Canis lupus familiaris* (dog) DGCR14 DNA sequence | 7 |
| *Canis lupus familiaris* DGCR14 protein sequence | 8 |
| *Felis catus* (cat) DGCR14 DNA sequence | 9 |
| *Felis catus* DGCR14 protein sequence | 10 |
| *Myotis lucifugus* (little brown bat) DGCR14 DNA sequence | 11 |
| *Myotis lucifugus* DGCR14 protein sequence | 12 |
| *Mus musculus* (mouse) DGCR14 DNA sequence | 13 |
| *Mus musculus* DGCR14 protein sequence | 14 |
| *Populus trichocarpa* (poplar) DGCR14 DNA sequence | 15 |
| *Populus trichocarpa* DGCR14 protein sequence | 16 |
| *Medicago truncatula* (barrelclover) DGCR14 DNA sequence | 17 |
| *Medicago truncatula* DGCR14 protein sequence | 18 |

Typically, genetically modified plant cells used in methods described herein constitute part or all of a whole plant. Such plants can be grown in a manner suitable for the species under consideration, either in a growth chamber, a greenhouse or in a field. Genetically modified plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a genetically modified plant can be grown and then selfed (or outcrossed and selfed) to obtain seeds homozygous for the nucleic acid construct. Alternatively, genetically modified plants can be propagated vegetatively for those species amenable to such techniques.

Genetically modified plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, genetically modified plant cells can be placed directly onto the medium or can be placed onto a filter film that is then placed in contact with the medium. When using liquid medium, genetically modified plant cells can be placed onto a flotation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

As used herein, the term "genetically modified plant tissue" refers to bith meristematic tissues and permanent (or non-meristematic) tissues of a genetically modified plant. In some embodiments, a genetically modified tissue comprises a dermal tissue, a vascular tissue or a ground tissue.

Methods of Improving Drought and Salt Tolerance in Plants

The inventors of the present disclosure have described a process of improving drought and salt tolerance/resistance in plants. Drought tolerance/resistance and salt tolerance/resistance, increased photosynthetic rate, biomass production and water-use efficiency are desirable qualities that affect plant biomass. With methods of this disclosure, it is possible to generate engineered plants which produce more biomass, and/or more crop and plant product derived thereof, if grown under conditions of low water availability/drought in comparison with plants not subjected to the method according to the present disclosure. In some embodiments, the biomass of the engineered plant is increased by at least 5%, by at least 10%, by at least 15%, by at least 20%, by at least 25%, by at least 30%, by at least 40%, by at least 50%, or by at least 60% when compared to a corresponding control plant.

In some embodiments, the method comprises introducing into a plant, plant cell or plant tissue an exogenous nucleic acid comprising a DiGeorge-Syndrome Critical Region 14 (DGCR14) gene, or a homolog thereof.

In some embodiments, the DGCR14 gene, or a homolog thereof, is from a plant. In some embodiments, the plant is *Arabidopsis*, poplar or barrelclover. In some embodiments, the DGCR14 gene, or a homolog thereof, is from an animal. In some embodiments, the DGCR14 gene is from a mammal. In some embodiments, the DGCR14 gene is selected from a mammal selected from the group consisting of a human, a mouse, a rat, a cat, a dog, a monkey, and a bat.

In some embodiments, the exogenous nucleic acid comprises a sequence with at least 90% sequence homology to a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, and SEQ ID NO: 17. In some embodiments, the exogenous nucleic acid encodes a protein with at least 90% sequence homology to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18.

In some embodiments a plant, plant cell or plant tissue can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed genetically modified plants and plant cells can be useful in the methods described herein.

Expression Vectors

The polynucleotides and expression vectors described herein can be used to increase the expression of a DiGeorge-Syndrome Critical Region 14 (DGCR14) gene product in plants and render them drought and salt resistant.

In some embodiments, the vector comprises a nucleic acid sequence encoding for a DGCR14 gene product from a plant. In some embodiments, the plant is *Arabidopsis*, poplar or barrelclover. In some embodiments, the DGCR14 gene, or a homolog thereof, is from an animal. In some embodiments, the DGCR14 gene is from a mammal. In some embodiments, the DGCR14 gene is selected from a mammal selected from the group consisting of a human, a mouse, a rat, a cat, a dog, a monkey, and a bat.

In some embodiments, the vector comprises a nucleic acid sequence with at least 90% sequence identity to a nucleotide sequence selected from the group consisting of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, and SEQ ID NO: 17. In some embodiments, the vector encodes a protein with at least 90% sequence identity to an amino acid sequence selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, and SEQ ID NO: 18.

The vectors provided herein can include origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

In some embodiments, the promoter to drive expression of genes of interest is a constitutive promoter. In some embodiments the constitutive promoter is selected from the group consisting of a ubiquitin promoter, a cauliflower mosaic virus (CaMV) 35S promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

In some embodiments, the promoter to drive expression of genes of interest is a regulated promoter. In some embodiments the regulated promoter is selected from the group consisting of a stress induced promoter, chemical-induced promoter, a light induced promoter, a dark-induced promoter, and a circadian-clock controlled promoter.

Some suitable regulatory regions initiate transcription, only or predominantly, in certain cell types. For instance, promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine chlorophyll a/b binding-6 (cab6) promoter (Yamamoto et al., 1994, *Plant Cell Physiol.*, 35:773-778), the chlorophyll a/b binding-1 (Cab-1) promoter from wheat (Fejes et al., 1990, *Plant Mol. Biol.*, 15:921-932), the chlorophyll a/b binding-1 (CAB-1) promoter from spinach (Lubberstedt et al., 1994, *Plant Physiol.*, 104:997-1006), the cab IR promoter from rice (Luan et al., 1992, *Plant Cell*, 4:971-981), the pyruvate orthophosphate dikinase (PPDK) promoter from corn (Matsuoka et al., 1993. *Proc. Natl. Acad. Sci. USA*, 90:9586-9590), the tobacco light-harvesting complex of photosystem (Lhcb1*2) promoter (Cerdan et al., 1997, *Plant Mol. Biol.*, 33:245-255), the *Arabidopsis* SUC2 sucrose-H+ symporter promoter (Truernit et al., 1995, *Planta*, 196:564-570) and thylakoid membrane protein promoters from spinach (psaD, psaF, psaE, PC, FNR, atpC, atpD, cab, rbcS).

In some embodiments, promoters of the instant application comprise inducible promoters. Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a vector, e.g., introns, enhancers, upstream activation regions, transcription terminators and inducible elements. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Techniques for introducing nucleic acids into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204,253, 6,329,571 and 6,013,863, incorporated herein by reference. If a cell or tissue culture is used as the recipient tissue for transformation, plants can be regenerated from transformed cultures if desired, by techniques known to those skilled in the art. See, e.g., Niu et al., 2000. *Plant Cell Rep.* V19:304-310; Chang and Yang, 1996, *Bot. Bull. Acad. Sin.*, V37:35-40 and Han et al., 1999, *Biotechnology in Agriculture and Forestry*, V44:291 (ed. by Y. P. S. Bajaj), Springer-Vernag.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1: Materials and Methods

Plant Materials and Constructs

*Arabidopsis* plants used in this study were grown in a growth chamber with 14 h light at 21° C./10 h dark at 18° C. with 60% relative humidity. The T-DNA insertional mutant dgcr14l-1 (SALK_096823) and dgcr14l-2 (SALK_009248) were obtained from the ABRC (https://abrc.osu.edu/). T-DNA insertions were analyzed by PCR using the following primers: SALK_096823 LP: 5'-GAACCTGCGATTGGAGTGTAG-3' (SEQ ID NO: 19), SALK_096823 RP: 5'-CAATCGAGAAGATCATCGAGC-3' (SEQ ID NO: 20), SALK_009248 LP: 5'-TGGAATGT-TATAGTGCGGTCC-3' (SEQ ID NO: 21), SALK_009248 RP: 5'-CGGATGAGAGTTCTCGATGAG-3' (SEQ ID NO: 22), and LBb1.3: 5'-ATTTTGCCGATTTCGGAAC-3' (SEQ ID NO: 23). The expression of DGCR14l in dgcr14l mutants was measured by qPCR using the following primers: DGCR14l qRT F: 5'-CATCTGATCAGCCACCGAGT-3' (SEQ ID NO: 24)) and DGCR14l qRT R: 5'-CTCAGT-TAAAGGCGCCTCAC-3' (SEQ ID NO: 25).

To express *Arabidopsis* DGCR14l (AT3G07790) and human DGCR14/ESS2 (NM_022719) in dgcr14l-1 mutant, DGCR14l and DGCR14/ESS2 were firstly cloned into pENTR vector (Invitrogen) and then subcloned into binary vector pGWB515 for transformation into dgcr14l-1 background. The expression of DGCR14l was measured by qPCR using DGCR14l qRT F: 5'-CATCTGATCAGC-CACCGAGT-3' (SEQ ID NO: 26) and DGCR14l qRT R: 5'-CTCAGTTAAAGGCGCCTCAC-3' (SEQ ID NO; 27) primers. The expression of DGCR14/ESS2 was measured by qPCR using DGCR14/ESS2 qRT F: 5'-GCG-GAGAGTGACGGAGAAT-3' (SEQ ID NO: 28) and DGCR14/ESS2 qRT R: 5'-CCCGGTCTGTGTACTTGCTG-3' (SEQ ID NO: 29) primers.

For subcellular localization analyses in protoplasts, DGCR14l, DGCR14/ESS2, and their mutant forms were firstly cloned into pENTR vector (Invitrogen) and then subcloned into transient expression vectors to fuse YFP to their C-terminal.

Phylogenetic Analysis

Multiple sequence alignment of the DGCR14 orthologs was conducted using MAFFT. Then the phylogenetic tree was inferred by using the maximum likelihood method and was conducted using the tool fasttree. Default parameters were used in MAFFT and fasttree.

RNA-Seq and Transcriptome Analysis

Total RNAs were extracted from three-week-old seedlings grown in soil. For each genotype, three replicates were prepared. RNAs were firstly qualified using Agilent 2100 Bioanalyzer. Stranded RNA-seq libraries were created and quantified by qPCR. Sequencing was performed using an Illumina HiSeq 4000 instrument. Raw fastq file reads were filtered and trimmed using the BGI software SOAPnuke.

To determine differentially expressed genes (DEGs), clean reads were mapped to *Arabidopsis* reference (TAIR10) using Bowtie2. DEGs were then detected by NOIseq with parameters of fold change>=2.00 and P value<0.01. Alternative splicing events and differential splicing events were identified using Multivariate Analysis of Transcript Splicing (MATS).

Salt Treatment

Seeds of various genotypes were germinated on ½ MS medium. For NaCl treatment, 4-day-old seedlings were transferred to ½ MS medium containing 200 mM of NaCl. After ten days, plant phenotypes were pictures and the survival rates were counted and calculated.

To detect gene expression changes induced by NaCl treatment, 7-day-old seedlings were transferred to ½ MS medium containing 200 mM of NaCl. After 4 hours, the treated seedlings were then sampled to extract total RNAs for qRT-PCR analysis.

Subcellular Localization and BiFC

Protoplast isolation and transfection were performed as previously described (Xie et al. (*The Plant Cell* 30, 1645-1660 (2018)). For subcellular localization, 8 µg of DGCR14l-YFP and DGCR14/ESS2-YFP constructs were co-transfected with 2 µg of the nuclear marker construct (mCherry-)VirD2NLS), respectively, into 100 µl of protoplasts (~2×10$^4$ cells) to determine their subcellular localizations. For colocalization, paired constructs (5 µg each) were co-transfected into 100 µl of protoplasts. For BiFC, paired genes were cloned into pSATI-nVenus-C (fuse with nVenus) and pSATI-cCFP-C (fuse with cCFP), respectively. Then their expression cassettes were cloned into pUC119 (pUC-RCS) vector using AscI for transient expression in protoplasts. The generated constructs (4 µl of nVenus construct and 4 µl of cCFP construct) were co-transfected with 2 µl of the nuclear marker construct (mCherry-VirD2NLS) into 100 µl of protoplasts. After 14 h incubation under weak light at room temperature, protoplasts were collected and resuspended in cold W5 solution (2 mM MES pH 5.7, 154 mM NaCl, 125 mM $CaCl_2$, and 5 mM KCl) to subject to microscopy. Images were collected using a Zeiss LSM 710 confocal microscope, equipped with 514 and 561 nm laser lines for excitation of YFP and mCherry, respectively. Images were processed using Zen software (Zeiss).

Conserved Amino Acid Analysis

The human DGCR14/ESS2 protein sequence was used as the query sequence for the BLASTP to identify orthologs in the NCBI non-redundant (nr) database. The top 500 sequences with identity >25.96% and covered 394 species were downloaded for further analysis. Multiple alignment of the 500 DGCR14 orthologs were performed using the Clustal X2.1, and the positions with sequence identity >99% were selected as conserved amino acids.

Accession Numbers

Sequence data from this article can be found under the following *Arabidopsis* Genome Initiative or National Center for Biotechnology Information accession numbers: *Arabidopsis* DGCR14l (AT3G07790), human DGCR14/ESS2 (NM_022719), U1-70 k (AT3G50670), U2B (AT2G30260), SWI3A (AT2G47620), KIN1(AT5G15960), COR15A (AT2G42540), P5CS2 (AT3G55610), KIN2 (AT5G15970), RD29B (AT5G52300), and RAB18 (AT5G66400).

Example 2

Plant and Mammal DGCR14 Orthologs have High Sequence Divergence

Figure 1C:
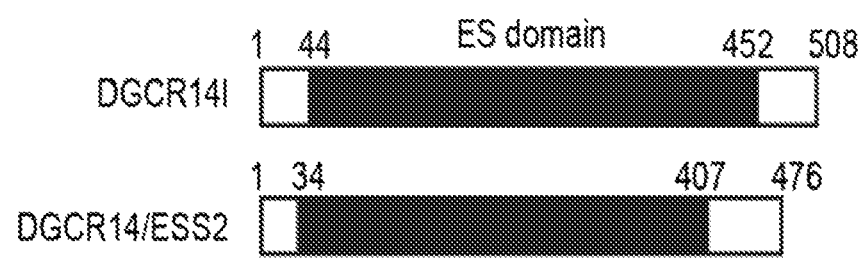

DGCR14 orthologs widely exist in plants, animals, and microbes. In most species, DGCR14 has a single copy. Phylogenetic analysis with DGCR14 orthologs from plant, animal, and microbe species showed that they can be divided into three subgroups: cluster I and II that exclusively contain animal species, and cluster III that contains plant and microbe species (FIG. 1A). The result that plant and animal DGCR14 orthologs belong to different clusters suggests the high divergence between them. As a model plant, *Arabidopsis* genome only contains one gene (AT3G07790) that encodes DGCR14 ortholog, which is named DGCR14-like (DGCR14l). DGCR14l and DGCR14/ESS2 proteins only share 26% identity (FIG. 1B). Despite the dramatic sequence divergence, the protein domain annotation by SMART (Simple Modular Architecture Research Tool) revealed that both DGCR14l and DGCR14/ESS2 proteins have a long ES domain (FIG. 1C), which is a coiled-coil region and widely conserved from yeast to human. However, the function of this ES domain remains unclear.

DGCR14l and DGCR14/ESS2 have the Same Subcellular Localization in Plant Cells

Figures 2A, 2B:
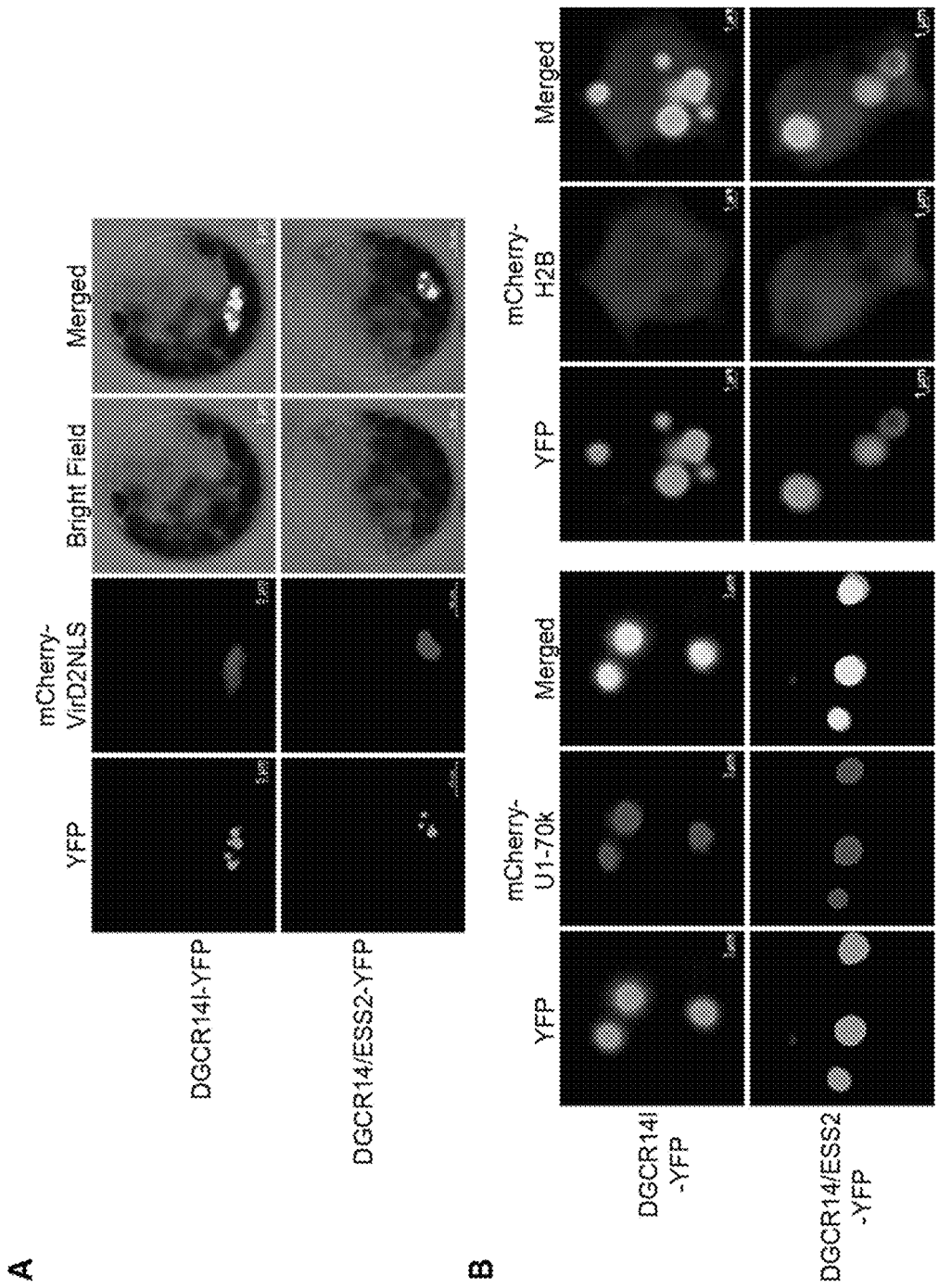
FIGS. 2A-2C. *Arabidopsis* and human DGCR14 orthologs have same subcellular localization pattern and protein-protein interaction partner in plant cells. (A) Subcellular localization of DGCR14l-YFP and DGCR14/ESS2-YFP (green color) in *Arabidopsis* leaf mesophyll protoplasts. The localization of the nucleus is indicated by the nuclear marker mCherry-VirD2NLS (red color). Scale bar: 5 (B) Co-localization of DGCR14l-YFP and DGCR14/ESS2-YFP (green color) with mCherry-U1-70 k and mCherry-H2B (red color), respectively, in *Arabidopsis* leaf mesophyll protoplasts. The co-localization of paired proteins is indicated by the yellow color in merged pictures. Scale bar: 1 (C) Bimolecular fluorescence complementation (BiFC) of cCFP-DGCR14l and cCFP-DGCR14/ESS2 (green color) with nVenus-U1-70 k and nVenus-H2B, respectively, in *Arabidopsis* leaf mesophyll protoplasts. The localization of the nucleus is indicated by the nuclear marker mCherry-VirD2NLS (red color). Scale bar: 5 μm.

The high sequence divergence between plant and mammal DGCR14 orthologs suggests that they may have distinct functions. To test this hypothesis, the inventors used *Arabidopsis* DGCR14l and human DGCR14/ESS2 for comparative studies. Since the localization in cellular compartments is one major determinant for protein function, the inventors firstly analyzed the subcellular localization of DGCR14l and DGCR14/ESS2 using the *Arabidopsis* mesophyll protoplast transient expression system. In the analysis, DGCR14l and DGCR14/ESS2 were each fused with Yellow Fluorescent Protein (YFP) at their C-terminal, and then transiently expressed in protoplasts. As shown in FIG. 2A, both DGCR14l-YFP and DGCR14/ESS2-YFP (green color) exhibit punctate distribution in the nucleus, which is indicated by overlapping with the red-colored nuclear marker mCherry-VirD2NLS. It is interesting to observe that DGCR14l and DGCR14/ESS2 have the same localization pattern, implying that the two orthologs may have similar, rather than distinct cellular functions.

DGCR14l and DGCR14/ESS2 are Associated with U1-70 k in the Nucleus

The punctate nuclear localization patterns of DGCR14l and DGCR14/ESS2 suggest that they may be associated with certain nuclear bodies that function in gene regulation and/or RNA processing, such as Cajal body (the hub for small nuclear ribonucleoprotein (snRNP) assembly and modification), polycomb body (the hub for gene repression), and nuclear speckle (the hub for pre-mRNA splicing), etc. By analyzing the co-localization of DGCR14 orthologs with nuclear body component markers, the inventors found that DGCR14l and DGCR14/ESS2 were co-localized with U1 SMALL NUCLEAR RIBONUCLEOPROTEIN-70K (U1-70 k, AT3G50670), which is a pre-mRNA spliceosome component. For the co-localization analysis, DGCR14l and DGCR14/ESS2 were fused with YFP tag (green color). Nuclear body markers were fused with mCherry tag (red color). Recombinant pairs of DGCR14 orthologs and nuclear body markers were co-transfected into protoplasts to determine their co-localization, which is indicated by overlapping of YFP and mCherry signals that shows yellow color. As shown in FIG. 2B, both DGCR14l and DGCR14/ESS2 co-localize with U1-70 k. However, the two DGCR14 orthologs have no co-localization with another pre-mRNA spliceosome marker, U2 SMALL NUCLEAR RIBONUCLEOPROTEIN B (U2B, AT2G30260). Given the fact that U1-70 k and U2B specifically associate with different small nuclear RNAs (snRNAs) in the spliceosome, these results suggest that DGCR14 may selectively associate with spliceosome components.

Figure 2C:
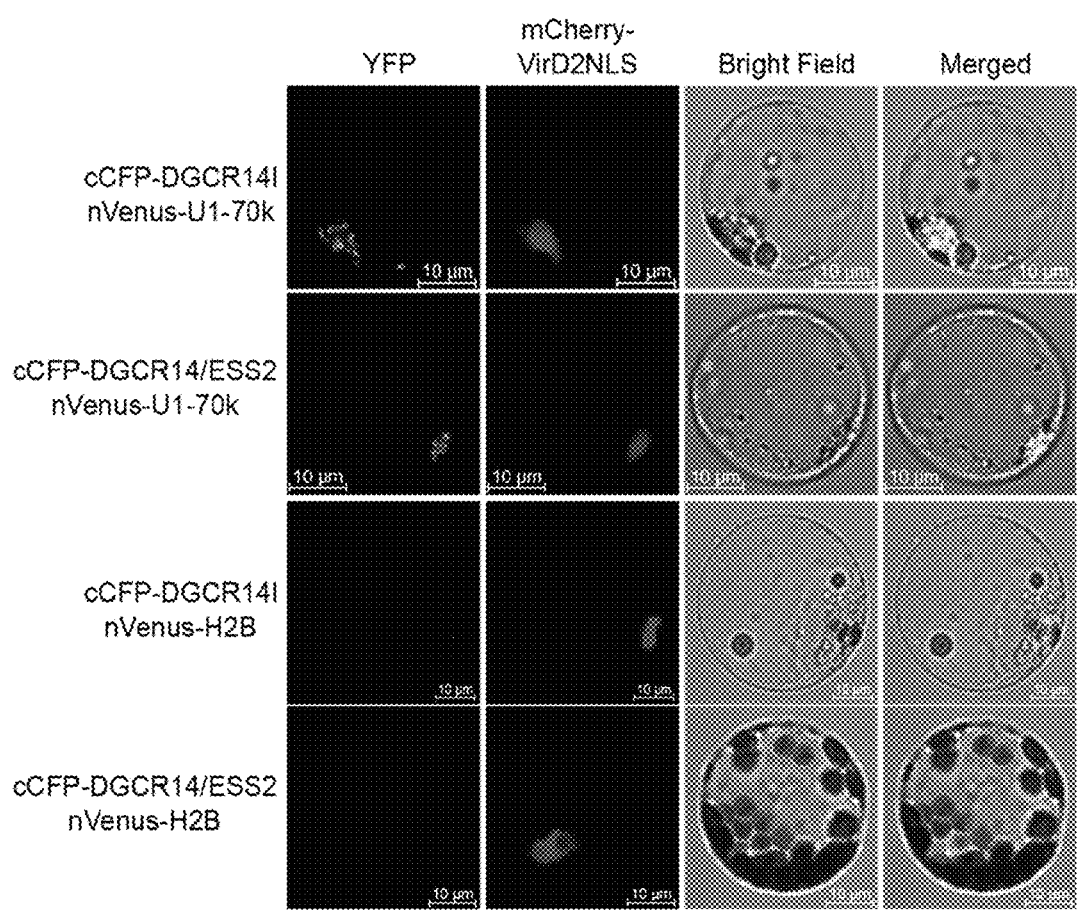

To further test the association of DGCR14l and DGCR14/ESS2 with spliceosome, a bimolecular fluorescence complementation (BiFC) assay was performed in *Arabidopsis* protoplasts. In this assay, DGCR14 orthologs and U1-70 k were fused with split YFP (C-terminal fragment of CFP (cCFP) and N-terminal of Venus (nVenus)), and co-expressed in protoplasts. The interaction between two proteins will bring cCFP and nVenus together to form a functional YFP, which then leads to fluorescence. As shown in FIG. 2C, YFP signals were detected in nuclear speckles for both DGCR14l-U1-70 k and DGCR14/ESS2-U1-70 k interactions. In contrast, no YFP signal was detected from DGCR14l-U2B or DGCR14/ESS2-U2B interaction (FIG. 2C), further supporting DGCR14's selectivity on spliceosome components. These results illustrate that both *Arabidopsis* DGCR14l and human DGCR14/ESS2 are associated with U1-70 k, which is specifically present in U1 small nuclear ribonucleoprotein (snRNP).

Example 3

Knockout of DGCR14 in *Arabidopsis* is Not Embryonically Lethal but Impairs Salt Stress Responses Having shown that DGCR14 orthologs share the similar cellular properties (i.e., subcellular localization and association with spliceosome component), the inventors wanted to further investigate whether *Arabidopsis* and human DGCR14 orthologs share similar biological functions despite their sequence divergence. To test this, the inventors analyzed *Arabidopsis* DGCR14l knockout mutants. Based on the cDNA sequence, DGCR14l gene contains one exon and no intron. The inventors obtained its T-DNA insertion lines SALK_096823 (dgcr14l-1) and SALK_009248 (dgcr14l-2) from the *Arabidopsis* stock center. T-DNA insertions in dgcr14l-1 and dgcr14l-2 mutants were validated by PCR using primers flanking the insertion sites in DGCR14l. RT-PCR analysis did not detect the transcripts of DGCR14l in dgcr14l-1 or dgcr14l-2, indicating that dgcr14l-1 and dgcr14l-2 mutants are likely null alleles. However, these two DGCR14 null alleles did not exhibit obvious deficiency in germination, vegetable growth, or reproductive growth (FIG. 3A), which is completely different from DGCR14 knockout in animal models (i.e., embryo lethality).

Figures 3A, 3B, 3C:
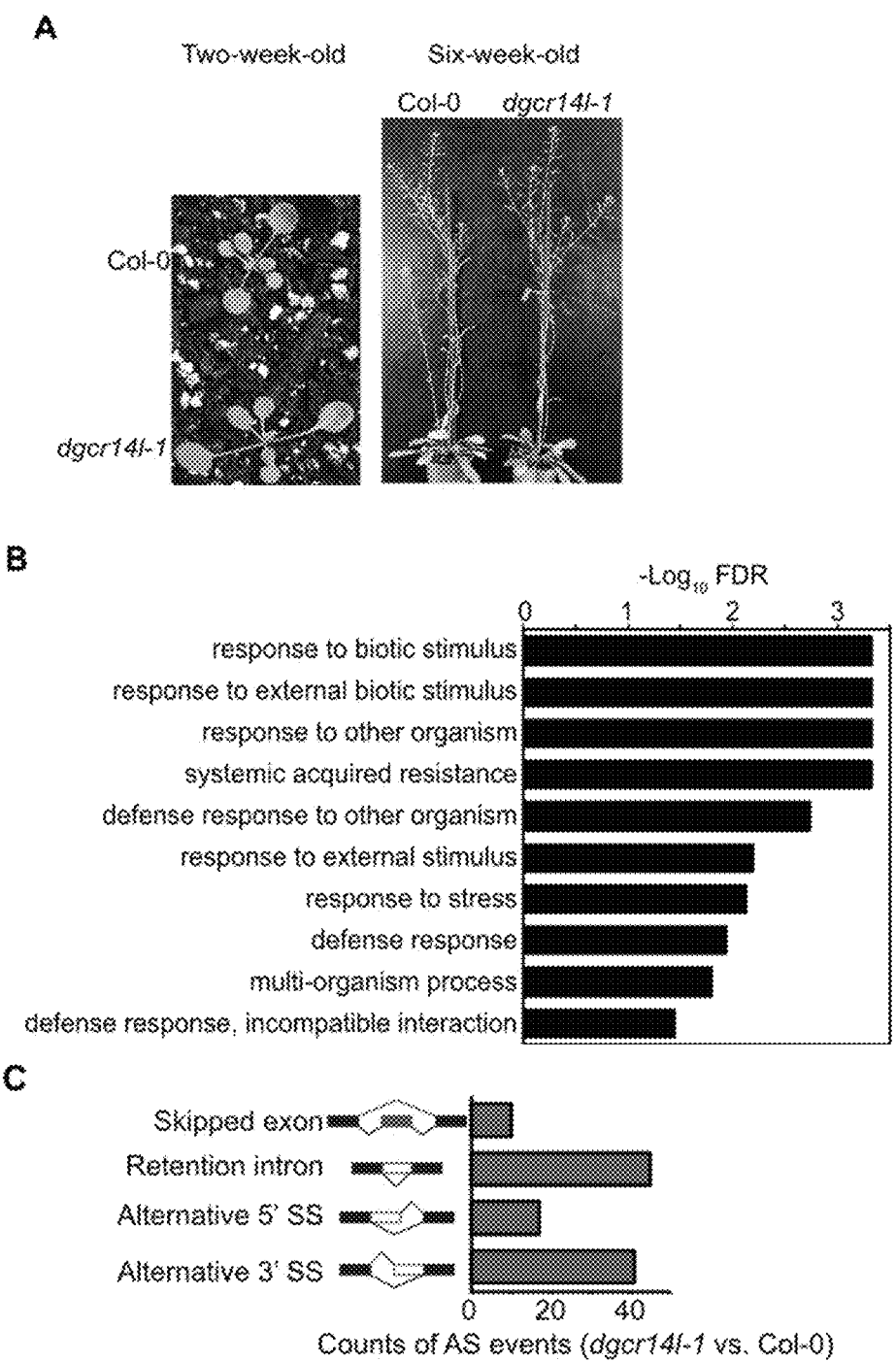
FIGS. 3A-3F. Disruption of DGCR14 in *Arabidopsis* does not affect plant growth but affects stress responses. (A) Phenotypes of two-week-old and six-week-old dgcr14l-1 and Col-0 (Wild-type). (B) GO terms enriched in differentially expressed genes in dgcr14l-1 mutant. FDR, False Discovery Rate. (C) The counts of pre-mRNA splicing events with significant differences between dgcr14l-1 mutant and Col-0. (D) Weblogo of the sequences around alternative splicing sites that were over-represented in dgcr14l-1 mutant. (E) Alternative splicing of SWI3A in Col-0 and dgcr14l-1 mutant. Transcriptome data of three biological replicates of Col-0 and dgcr14l-1 mutant was visualized by IGV browser. (F) PCR analysis showing the increased retention intron (RI) of SWI3A gene in dgcr14l-1 mutant under control (—NaCl) and salt stress (+NaCl) conditions. EF1α was amplified as a quantity control.

To fully explore the biological consequences of DGCR14 knockout in *Arabidopsis*, the inventors performed transcriptomics analysis using RNAs from three-week-old dgcr14l mutants and its corresponding wild type Col-0. Three biological replicates were analyzed, and highly consistent results among replicates were obtained (Pearson correlation value≥0.97). The differential gene expression analysis identified a total of 314 genes whose transcription has significant changes (P value<0.01, false discovery rate [FDR]<0.05) in dgcr14l-1 mutant, including 225 up-regulated genes and 89 down-regulated genes. The inventors then performed Gene Ontology (GO) enrichment analysis to determine biological processes that are dramatically affected by DGCR14 depletion as a way to deduce the function of DGCR14. As shown in FIG. 3B, nine out of the top ten GO terms are related with plant defense, including response to biotic stimulus (GO: 0009607), response to external biotic stimulus (GO: 0043207), response to other organism (GO:0051707), systemic acquired resistance (GO:0009627), defense response to other organism (GO:0098542), response to external stimulus (GO:0009605), response to stress (GO:0006950), and defense response (GO:0006952). The GO enrichment analysis of dgcr14l-2 mutant has similar outcomes as dgcr14l-1. These GO enrichment results suggest that DGCR14l may play an active role in plant defense mechanisms. Because dgcr14l-1 and dgcr14l-2 have similar GO enrichment outcomes and their T-DNA insertion sites are very close, the inventors selected dgcr14ll-1 for following analyses.

Figure 3D:
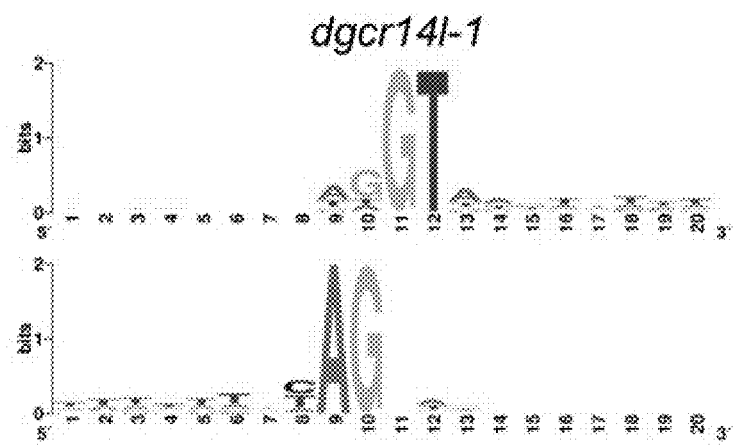
Figure 3E:
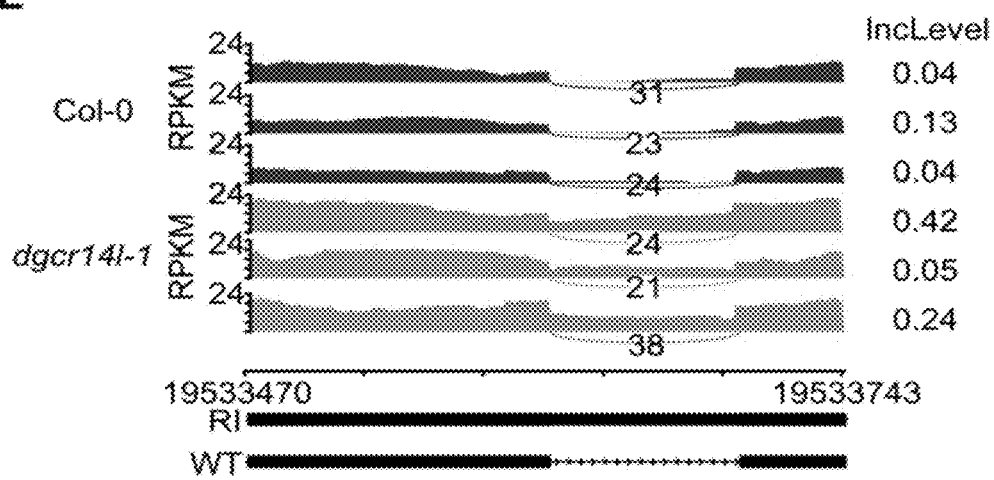
Figure 3F:
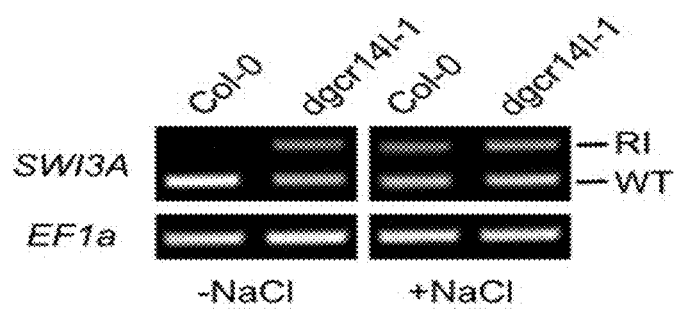
Figures 6A, 6B:
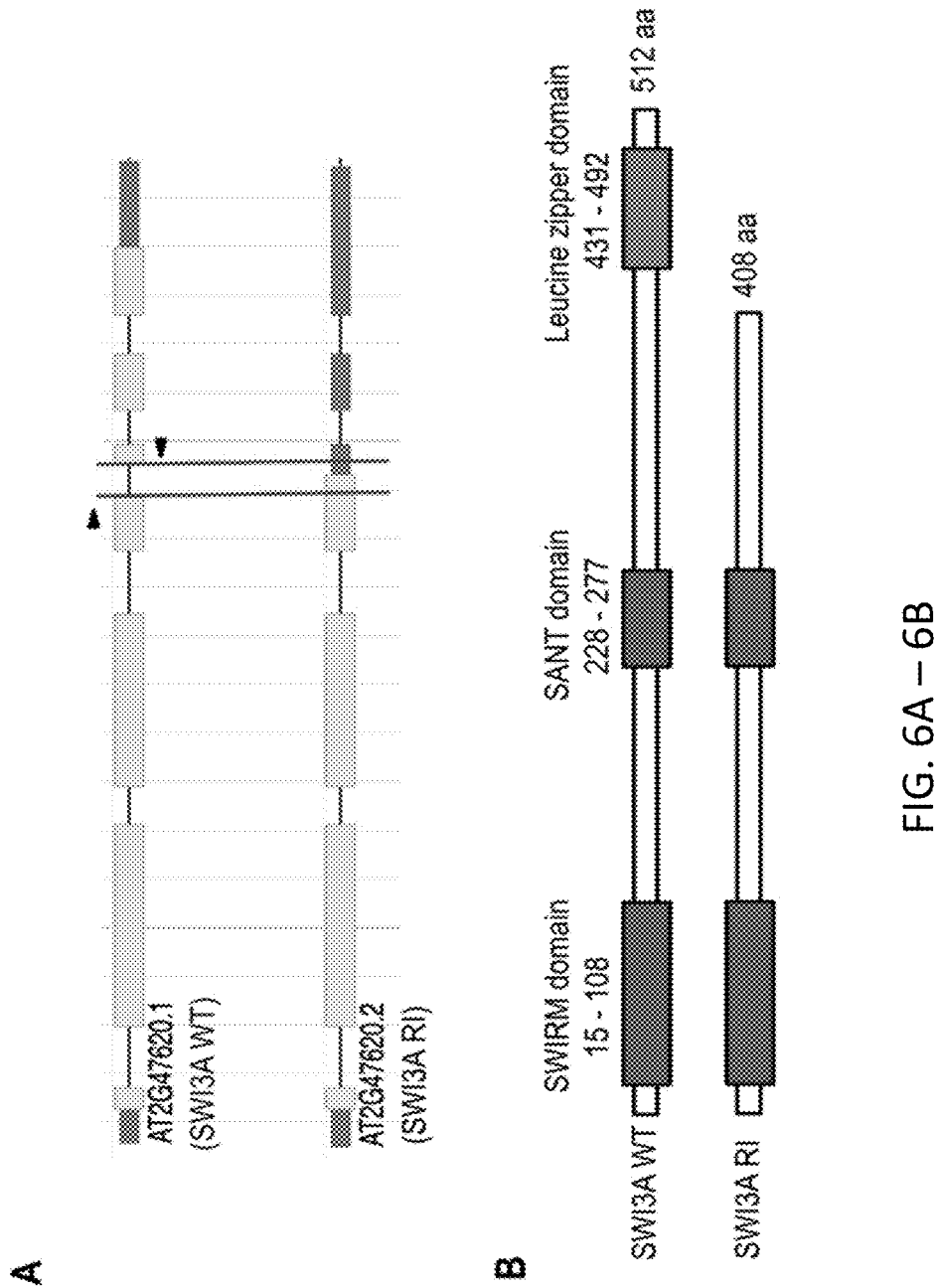
FIGS. 6A-6B. Retention intron of SWI3A triggers the deletion of the C-terminal leucine zipper domain. (A) Scheme of the wild-type SWI3A (SWI3A WT) and retention intron SWI3A (SWI3A RI). The retention intron region is indicated by red lines; Primers used for PCR validation are indicated by black arrows. (B) Scheme of SWI3A domain deletion caused by retention intron.

Because the inventors have shown that *Arabidopsis* and human DGCR14 orthologs are associated with spliceosome component, the inventors also wanted to examine alternative splicing (AS) events in dgcr14l-1 mutant. Multivariate Analysis of Transcript Splicing (MATS) was used to identify alternative splicing events and differential splicing events from RNA-seq data. Compared with Col-0, dgcr14l-1 mutant has 113 significantly changed AS events (P<0.1), including 41 of alternative 3' splicing sites (SSs), 17 of alternative 5' SSs, 45 of retention intron, and 10 of skipped exon (FIG. 3C). Sequence analysis of these over-represented alternative splicing events revealed that these activated splice sites were still associated with GU and AG dinucleotides (FIG. 3D), suggesting that the depletion of DGCR14 did not change the accuracy of the sequence recognition of the splicing sites but simply alter the frequency of AS. Because of the broad impact of DGCR14 knockout on the expression of over 300 *Arabidopsis* genes, the inventors wanted to further examine if essential transcriptional regulators are among those 113 genes with significantly changed AS events. The inventors discovered that a core subunit of SWITCH/SUCROSE NONFERMENTING (SWI/SNF) chromatin-remodeling complexes named SWI3A, had aberrant pre-mRNA splicing in dgcr14l-1 mutant (FIG. 3E). SWI/SNF chromatin-remodeling complexes are important transcriptional regulators in eukaryotes. In dgcr14l-1, SWI3A had increased retention intron events that trigger the deletion of the C-terminal leucine zipper domain (FIG. 6), which is functional in protein-protein interactions for complex assembly. The increased retention intron of SWI3A was further validated by PCR using primers flanking the retained intron (FIG. 6A). As shown in FIG. 3F, the band of retention intron was only detected in dgcr14l-1 mutant, but not in Col-0.

To validate the effect of DGCR14 disruption on plant salt stress responses, the inventors transferred four-day-old Col-0 and dgcr14l-1 seedlings onto ½ MS plate containing 200 mM of NaCl for salt stress treatment and found that the dgcr14l-1 mutant is more susceptible towards salt stress than Col-0. After ten days, the survived (green leaves) and dead seedlings (white leaves) were counted to calculate the survival rate. After NaCl treatment, the survival rate of the dgcr14l-1 mutant (47.83%, n=50) is much lower than that of Col-0 (69.23%, n=50) (FIG. 4A), demonstrating that the dgcr14l-1 mutant has a reduced tolerance towards salt stress.

Figures 4A, 4B, 4C, 4D:
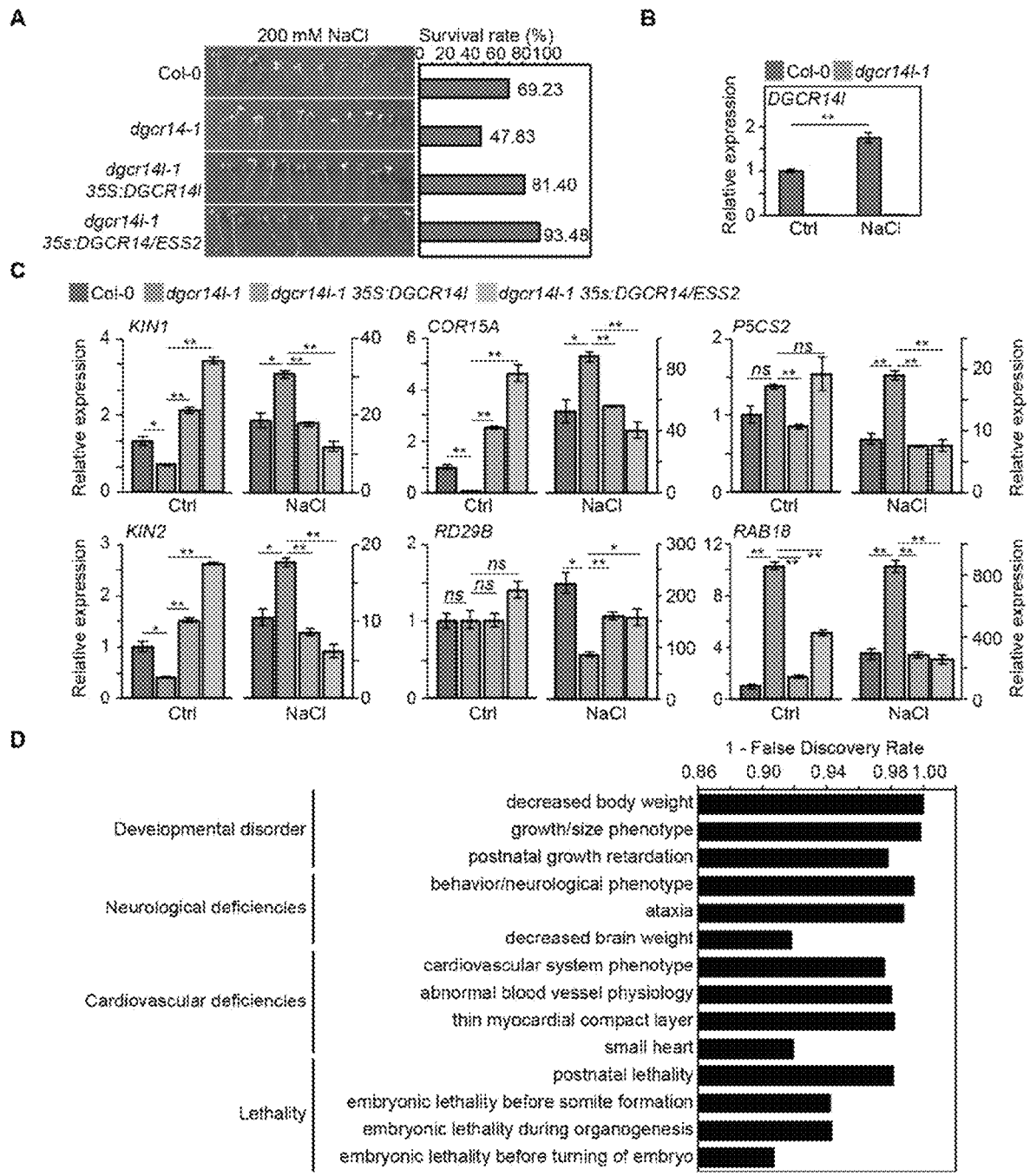
FIGS. 4A-4D. dgcr14l-1 mutant is deficient in salt stress responses. (A) Phenotypes and survival rates of Col-0, dgcr14l-1, dgcr14l-1 35S:DGCR14l, and dgcr14l-1 35S: DGCR14/ESS2 plants after 200 mM NaCl treatment for ten days. Values represent means±SEM, n=50. (B) qRT-PCR analysis showing NaCl-induced DGCR14l expression. Gene expressions were normalized against the expression of EF1α. DGCR14l expression in Col-0 without NaCl treatment was set as 1. Values represent means±SEM, n=3. (C) qPCR analysis showing expression changes of KIN1, COR15A, P5CS2, KIN2, RD29B, and RAB18 in Col-0, dgcr14l-1, dgcr14l-1 35S: DGCR14l, and dgcr14l-1 35s: DGCR14/ESS2 with or without NaCl treatment. Gene expression in Col-0 without NaCl treatment was set as 1. Values represent means±SEM, n=3. (D) Orthologous phenotypes of plant salt stress responses in mouse (Data is from Phenologs database).

To further validate the role of DGCR14l in salt stress responses, the inventors measured the expression of DGCR14l in Col-0 under control and salt stress conditions. As shown in FIG. 4B, DGCR14l expression was induced by NaCl treatment. The inventors also validated the RNA-seq data with qRT-PCR for two salt stress-responsive marker genes: KIN1, which encodes a protein kinase induced by cold or dehydration treatment and COR15A, which encodes a chloroplast protein protecting stromal proteins from aggregation under abiotic stresses. Consistent with the RNA-seq data, the two genes had reduced expression levels in dgcr14l-1 mutant under the control condition (FIG. 4C) whereas salt-induced KIN1 and COR15A expressions were increased significantly in dgcr14l-1 mutant (FIG. 4C). In addition, the inventors observed varied salt-induced expressions of other marker genes, including P5CS2, KIN2, RD29B, and RAB18. The qPT-PCR analyses revealed that dgcr14l-1 mutant exhibited higher salt-induced expressions of P5CS2, KIN2, and RAB18 than those in Col-0 (FIG. 4C). In contrast, salt-induced RD29B expression was reduced in dgcr14l-1 mutant (FIG. 4C). The inventors also observed the induction of retention intron of SWI3A gene by NaCl treatment (FIG. 3F), suggesting that the alternative splicing of SWI3A could be associated with salt stress responses.

Collectively, the physiological and gene expression analyses of the instant disclosure demonstrated that DGCR14 is required for proper salt stress responses.

Example 4

Both Plant and Human DGCR14 can Complement Salt Stress Phenotypes of dgcr14l-1 Mutant To validate the involvement of DGCR14l in plant salt stress responses, the inventors over-expressed DGCR14l gene in dgcr14l-1 mutant (dgcr14l-1 35S:DGCR14l) and measured salt stress tolerance of genetically modified plants.

dgcr14l-1 35S:DGCR14l plants exhibited a survival rate of 81.40% (n=50), which is even higher than that of Col-0 (FIG. 4A). Meanwhile DGCR14l over-expression was capable of complementing the aberrant expression of KIN1, COR15A, P5CS2, KIN2, RD29B, and RAB18 in dgcr14l-1 mutant under both control and salt stress conditions (FIG. 4C), further support that that DGCR14l is involved in plant salt stress responses as well as associated stress-responsive gene expression.

Having defined salt stress susceptibility as a scoreable phenotype of dfcr14 mutant, the inventors wanted to use this to test the conservation/difference of biological function between *Arabidopsis* and human DGCR14 orthologs. The inventors over-expressed human DGCR14/ESS2 gene in the dgcr14l-1 mutant (dgcr14l-1 35S:DGCR14/ESS2) in a same manner as the *Arabidopsis* DGCR14 overexpression. Interestingly, the inventors observed the complementation of salt stress phenotypes by human DGCR14 as the over-expression of *Arabidopsis* DGCR14l did. As shown in FIG. 4A, dgcr14l-1 35S:DGCR14/ESS2 plants had a survival rate of 93.48% under NaCl treatment, which is even higher than the over-expression of DGCR14l. Moreover, the over-expression of DGCR14/ESS2 displayed similar effects as *Arabidopsis* DGCR14 on the expression of KIN1, COR15A, P5CS2, KIN2, RD29B, and RAB18. (FIG. 4C).

These results suggest that *Arabidopsis* and human DGCR14 orthologs has similar biological functions. On the other hand, the depletion of conserved orthologs with the same function often manifests different phenotypic outputs in different organisms because of the organism-specific roles played by the orthologs. To explore the connection between reduced salt stress tolerance of *Arabidopsis* DGCR14l null mutant and lethality of DGCR14 knockout mammals, the inventors searched *Arabidopsis* salt stress response in the Phenologs database, which enabled to identify cross-organism pairs of orthologous phenotypes that significantly share common orthologous genes. By doing so, the inventors found that response to salt stress in *Arabidopsis* has orthologous phenotypes in mouse that are associated with developmental disorders, lethality, and neurological & cardiovascular deficiencies (FIG. 4D). This discovery may explain the phenotypic difference of DGCR14 knockout in *Arabidopsis* and mammals.

*Arabidopsis* and Human DGCR14 Orthologs Share a Functional Motif

Although *Arabidopsis* DGCR14l and human DGCR14/ESS2 protein only have 26% identity at the amino acid level, the instant studies using the model plant *Arabidopsis* demonstrated that the two DGCR14 orthologs still have conserved molecular and biological functions when tested in the *Arabidopsis* model. These discoveries implied that these two proteins may share similar functional motifs despite high divergence in the amino acid sequence. In order to search for potential conserved motifs, the inventors performed protein sequence alignment using 500 DGCR14 orthologs from 395 plant, animal, and microbe species. The conservation rate of each amino acid was calculated by counting the percentage of orthologs containing the same amino acid in a total of 500 DGCR14 orthologs. By using 99% as the cutoff, the inventors discovered four highly conserved amino acids. Three out of four amino acids are adjacent and form a small motif (TWG) in both *Arabidopsis* DGCR14l (aa364-366) and human DGCR14/ESS2 (aa317-319). The other single conserved amino acid is also present in DGCR14l (P372) and DGCR14/ESS2 (P325).

Figure 5:
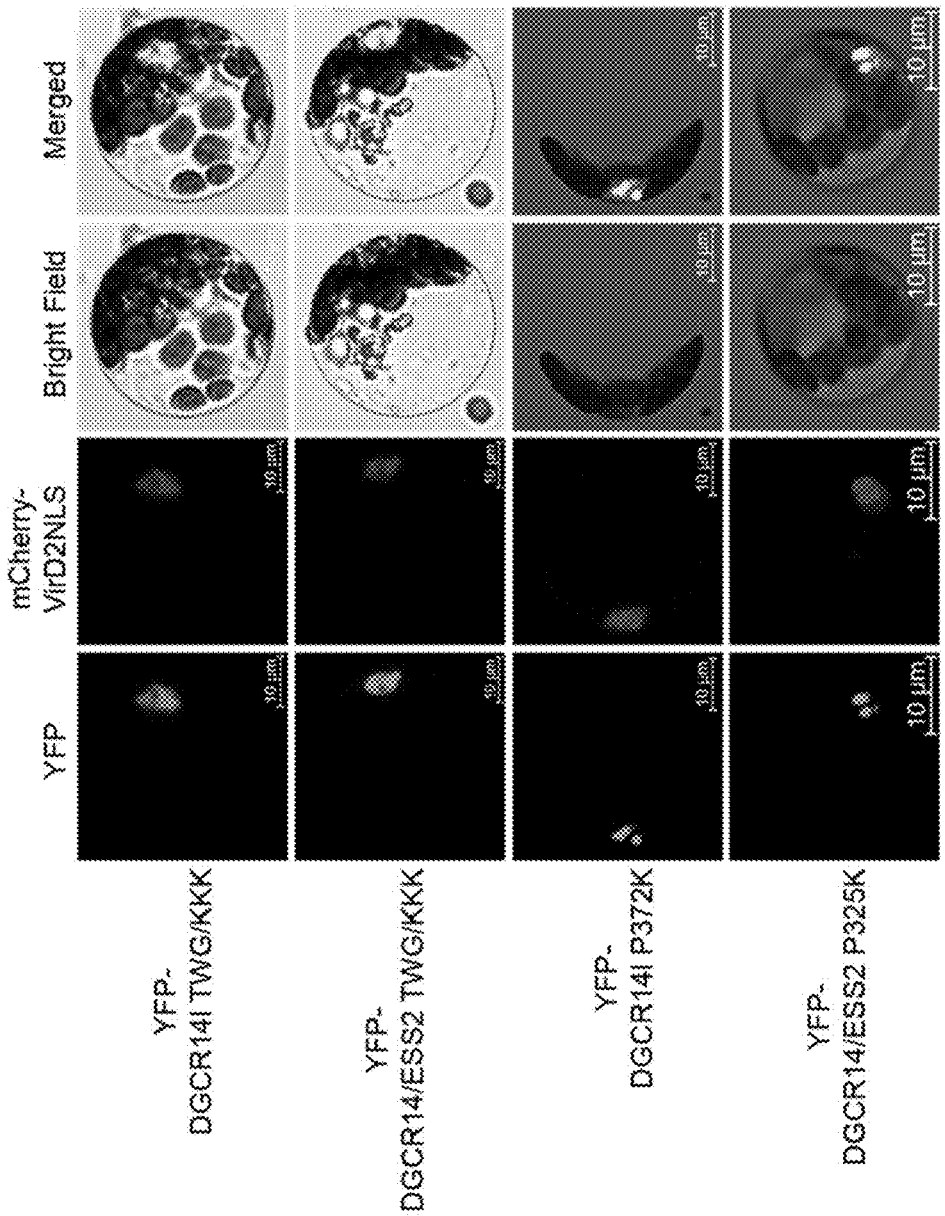
FIG. 5. The motif shared by *Arabidopsis* and human DGCR14 orthologs is critical for their subcellular localization. Subcellular localization of DGCR14l and DGCR14/ESS2 containing different amino acid substitutions. The localization of the nucleus is indicated by the nuclear marker mCherry-VirD2NLS (red color). Scale bar: 10 μm.

To explore the potential functionality of these four conserved amino acids, the inventors introduced two mutations into DGCR14l and DGCR14/ESS2 proteins: one mutation is a substitution of TWG with KKK (DGCR14l TWG/KKK and DGCR14/ESS2 TWG/KKK) and the other mutation is a substitution of P with K (DGCR14l P372K and DGCR14/ESS2 P325K). These radical amino acid substitutions are expected to alter DGCR14 protein function due to the difference in their chemical properties (polar vs. non-polar etc.). Then, mutated DGCR14l and DGCR14/ESS2 proteins were fused with YFP tag to investigate their subcellular localizations in protoplasts. As shown in FIG. 5, DGCR14l TWG/KKK and DGCR14/ESS2 TWG/KKK exhibited significantly altered localization patterns in which their signals spread to the whole nucleus instead of concentrating in nuclear speckles. In contrast, the substitution of P with K (DGCR14l P372K and DGCR14/ESS2 P325K) had no effect on the localization patterns of DGCR14l or DGCR14/ESS2. These results demonstrated that the TWG motif shared by *Arabidopsis* and human DGCR14 orthologs is critical for their proper nuclear localization.

Example 5

DGCR14 is an ancient protein that widely exists in plants, animals, and microbes. In animal models, DGCR14 depletion is associated with developmental disorders and embryonic lethality. In plants, the inventors found that DGCR14 is required for proper abiotic stress responses, which are crucial for plant survival and development. Generally, proteins with only 26% sequence identity are considered to have totally different functions. However, the inventors' studies on *Arabidopsis* and human DGCR14 orthologs revealed that they have conserved molecular and biological functions. The two DGCR14 orthologs have the same nuclear distribution pattern and are associated with the same protein partner U1-70 k, when tested in plant cells. Moreover, both of them can restore salt stress tolerance and salt stress-responsive genes expression of dgcr14l-1 mutant. In human cells, DGCR14/ESS2 has been reported to selectively associate with small nuclear RNAs (snRNAs) that mediate pre-mRNA splicing, including U1, U4, and U6 snRNAs. In plant cells, the inventors found that DGCR14l and DGCR14/ESS2 are associated with U1-70 k, but not U2B. U1-70 k is only present in the U1 small nuclear ribonucleoprotein (snRNP) that specifically associates with U1 snRNA, whereas U2B is a U2 snRNP-specific protein. Thus, the instant disclosure suggests that the selective association with snRNPs may determine DGCR14's specificity in snRNAs. On the other hand, the sequence divergence and functional conservation between *Arabidopsis* and human DGCR14 orthologs prompted the inventors to hypothesize that over millions of years of divergent evolution between plants and animals did not change essential motifs in crucial proteins like DGCR14. To support this hypothesis, the inventors identified a functional motif shared by *Arabidopsis* and human DGCR14 orthologs. Although the motif only contains three amino acids, the inventors discovered that this motif is critical for the proper subcellular localization of DGCR14 orthologs. This study demonstrates the value of cross-kingdom comparative studies in understanding the sequence-function relationship.

The different depletion phenotypic outcomes of orthologs with conserved function in plants and animals have been observed and systematically characterized in previous studies. The phenotypic difference makes plants a good alternative platform to study mechanisms of fatal diseases in human. DGCR14 was named as DiGeorge-syndrome Critical Region 14 because of its tight association with a set of developmental disorders caused by 22q11.2 deletion in human. The lethality of DGCR14/ESS2 knockout in mouse prevented the comprehensive study of DGCR14/ESS2 biological function. In contrast, the knockout of DGCR14 in *Arabidopsis* has a limited effect on plant growth and development, which enabled the inventors to gain new insights into DGCR14 function using DGCR14 depletion *Arabidopsis*. The transcriptomic and physiological studies on *Arabidopsis* DGCR14l null mutants revealed that DGCR14 is required for plant salt stress response, which has orthologous phenotypes in mouse that are related with developmental disorders, lethality, and neurological & cardiovascular deficiencies. It is notable that these mouse phenotypes highly overlap with symptoms of human DiGeorge syndrome (or 22q11.2 deletion syndrome), including developmental delay, heart defects, and learning problems. At the molecular level, the inventors found that DGCR14 is required for the proper pre-mRNA splicing of SWI3A in *Arabidopsis*. SWI3A is a core subunit of SWI/SNF chromatin-remodeling complexes. In plants, SWI/SNF complexes are critical for the transcriptional regulation of various biological processes, including development, growth and abiotic stress responses. More importantly, components of SWI/SNF chromatin-remodeling complexes, as well as the regulatory mechanisms they are involved in, are highly conserved across eukaryotic species including *Arabidopsis* and human. In mammals, mutations that interfere SWI/SNF complexes function have been shown to lead to abnormal cell cycle progression, tumorigenesis and early lethality, which are phenotypes also been observed in 22q11.2 deletion. Therefore, the inventors speculate that 22q11.2 deletion in human may disrupt crucial and conserved mechanisms associated with DGCR14, such as SWI/SNF complex-mediated transcriptional regulation, to cause developmental disorders.

DGCR14/ESS2 has been reported to physically interact with RORγ to enhance its transcriptional activation in animal cells. In conclusion, the instant studies on *Arabidopsis* and human DGCR14 orthologs demonstrate that plants can be a valuable alternative platform to understand mechanisms of human fatal diseases and comparative studies across plant and animal kingdoms provide a better understanding of the sequence-function relationship.

What is claimed is:

1. A genetically modified plant, plant cell or plant tissue, wherein an exogenous nucleic acid comprising a DiGeorge-Syndrome Critical Region 14 (DGCR14) gene is expressed in the plant, plant cell or plant tissue;
   wherein the DGCR14 gene encodes a protein comprising a TWG amino acid motif and an amino acid sequence selected from the group consisting of SEQ ID NO: 2, SEQ ID NO: 4, SEQ ID NO: 16, and SEQ ID NO: 18;
   wherein the DGCR14 gene is under the control of a heterologous promoter; and
   wherein the expression of the DGCR14 gene improves drought and salt resistance in the plant, plant cell or plant tissue.

2. The genetically modified plant, plant cell or plant tissue of claim 1, wherein the DGCR14 gene comprises a nucleotide sequence selected from the group consisting of SEQ ID NO: 1, SEQ ID NO: 3, SEQ ID NO: 15, and SEQ ID NO: 17.

3. The genetically modified plant, plant cell or plant tissue of claim 1, wherein the exogenous nucleic acid is stably integrated into the plant genome.

4. The genetically modified plant, plant cell or plant tissue of claim 1, wherein the plant is a monocot or a dicot.

5. The genetically modified plant, plant cell or plant tissue of claim 1, wherein the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea,* and *Zoysia.*

6. A method of improving drought and salt resistance in a plant, plant cell or plant tissue comprising: expressing a DiGeorge-Syndrome Critical Region 14 (DGCR14) gene from an exogenous nucleic acid in the plant, plant cell or plant tissue;
   wherein the DGCR14 gene encodes a protein comprising a TWG amino acid motif and an amino acid sequence selected from the group consisting of SEQ ID NO: 2, SEQ ID NO: 4, SEQ ID NO: 16, and SEQ ID NO: 18; and
   wherein the DGCR14 gene is under the control of a heterologous promoter.

7. The method of claim 6, wherein the DGCR14 gene comprises a nucleotide sequence selected from the group consisting of SEQ ID NO: 1, SEQ ID NO: 3, SEQ ID NO: 15, and SEQ ID NO: 17.

8. The method of claim 6, wherein the exogenous nucleic acid is stably integrated into the plant genome.

9. The method of claim 6, wherein the plant is a monocot or a dicot.

10. The method of claim 1, wherein the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea,* and *Zoysia.*

\* \* \* \* \*

SEQUENCE LISTING

```
<160> NUMBER OF SEQ ID NOS: 29

<210> SEQ ID NO 1
<211> LENGTH: 1527
<212> TYPE: DNA
<213> ORGANISM: Arabidopsis thaliana

<400> SEQUENCE: 1
atgtttcttt cacctggtca ttctcctcgt cagatttctt ctccatcgcc gtcttcttat      60
tccgatgata ccctccgatc aacgcctcgc agttcttcct cggagatcat tcctcgaaac     120
cctagaaaac ggatgagagt tctcgatgag gacgcttatg ttgaagcaat cgagaagatc     180
atcgagcgtg attactttcc agatataact aagcttaggg atcggctcga ttggatccaa     240
gcggtgaaaa cccgtgaccc gattcaaatc cgagatgccc agttgaagat tatcgagagg     300
cgtggaaaga aggcgaatca tcatgttgga gataccgagg gtaaaactca aactcctgga     360
tctacttttc tgagaaattt cactcctttta gatgaatttg atggtaaaac ccctagaact     420
cctggagtat ctggtagaga atttcatggt gttgaagtag atgctggtga tggagatgaa     480
gatatagatc ttaatttgtc cctagatgag ttctttagga gatatactag tgaggataac     540
gagagctttt cgaagattct tgagaaggta aataggaaga agaaggagaa gtatggcttt     600
ctccttgaag gtgaaaagga ggatggtaaa tctattgagg atgtgaagag agataggatt     660
acagatgggt atggtacatc tgatcagcca ccgagtactt tagaaggatg gaaatatacg     720
gcgaagaatc ttctgatgta ccatccagct gatcggggtg aggcgccttt aactgaggcg     780
gaaagggcag tgagattact tggattgact aaggagatag ttaaagggaa cactcgtttt     840
catggtaaga ctatggattc taggccaaga gaagatggtt ctgttgagat tctctacact     900
ccaatcgcag gttcttcccc gatgcatatc tcaggtaggg acagagacaa gtctaaaagg     960
tatgatcttg atgatctaag gaaaacaccg aatcctttct atgtggaatc agataagagg    1020
gcagacaatg ggtatagttt tgttagaacg ccttctcctg ctccaggtct tgatgaatca    1080
ccctttataa catggggtga gattgatggg acaccaatgc gattagatct tgaggataca    1140
cctattgata ttggtggtag tgctgatgga ccgcactata acattccatc tgcacctcct    1200
agagatgtaa gggcacattc attatcaagg gatgcatcgc gaaaacttag agagagatcg    1260
```

```
aatagtatgt ttaagaaacc tccgttgcca tctcctcatc gaagtggaag tgcaagtccg    1320
aatgttagga ctctttcacc cgctgctcag aagttttca gaaaggcaat agctaaatca     1380
```

```
aatagtatgt ttaagaaacc tccgttgcca tctcctcatc gaagtggaag tgcaagtccg    1320
aatgttagga ctctttcacc cgctgctcag aagttttca  gaaaggcaat agctaaatca    1380
tcttctactg ttgatgagag ccttcgtgca agttatcgtg gagcaagtcc tcgtggagca    1440
agtcctggtg ctgtgactcc taagagtgtg agaagtattt caagatttgg caaagatggg    1500
accagctcag agacaaggtc gccttga                                        1527
```

<210> SEQ ID NO 2
<211> LENGTH: 508
<212> TYPE: PRT
<213> ORGANISM: Arabidopsis thaliana

<400> SEQUENCE: 2

```
Met Phe Leu Ser Pro Gly His Ser Pro Arg Gln Ile Ser Ser Pro Ser
1               5                   10                  15

Pro Ser Ser Tyr Ser Asp Asp Thr Leu Arg Ser Thr Pro Arg Ser Ser
            20                  25                  30

Ser Ser Glu Ile Ile Pro Arg Asn Pro Arg Lys Arg Met Arg Val Leu
        35                  40                  45

Asp Glu Asp Ala Tyr Val Glu Ala Ile Glu Lys Ile Ile Glu Arg Asp
    50                  55                  60

Tyr Phe Pro Asp Ile Thr Lys Leu Arg Asp Arg Leu Asp Trp Ile Gln
65                  70                  75                  80

Ala Val Lys Thr Arg Asp Pro Ile Gln Ile Arg Asp Ala Gln Leu Lys
                85                  90                  95

Ile Ile Glu Arg Arg Gly Lys Lys Ala Asn His His Val Gly Asp Thr
            100                 105                 110

Glu Gly Lys Thr Gln Thr Pro Gly Ser Thr Phe Leu Arg Asn Phe Thr
        115                 120                 125

Pro Leu Asp Glu Phe Asp Gly Lys Thr Pro Arg Thr Pro Gly Val Ser
    130                 135                 140

Gly Arg Glu Phe His Gly Val Glu Val Asp Ala Gly Asp Gly Asp Glu
145                 150                 155                 160

Asp Ile Asp Leu Asn Leu Ser Leu Asp Glu Phe Phe Arg Arg Tyr Thr
                165                 170                 175

Ser Glu Asp Asn Glu Ser Phe Ser Lys Ile Leu Glu Lys Val Asn Arg
            180                 185                 190

Lys Lys Lys Glu Lys Tyr Gly Phe Leu Leu Glu Gly Glu Lys Glu Asp
        195                 200                 205

Gly Lys Ser Ile Glu Asp Val Lys Arg Asp Arg Ile Thr Asp Gly Tyr
    210                 215                 220

Gly Thr Ser Asp Gln Pro Pro Ser Thr Leu Glu Gly Trp Lys Tyr Thr
225                 230                 235                 240

Ala Lys Asn Leu Leu Met Tyr His Pro Ala Asp Arg Gly Glu Ala Pro
                245                 250                 255

Leu Thr Glu Ala Glu Arg Ala Val Arg Leu Leu Gly Leu Thr Lys Glu
            260                 265                 270

Ile Val Lys Gly Asn Thr Arg Phe His Gly Lys Thr Met Asp Ser Arg
        275                 280                 285

Pro Arg Glu Asp Gly Ser Val Glu Ile Leu Tyr Thr Pro Ile Ala Gly
    290                 295                 300

Ser Ser Pro Met His Ile Ser Gly Arg Asp Arg Asp Lys Ser Lys Arg
305                 310                 315                 320
```

Tyr Asp Leu Asp Asp Leu Arg Lys Thr Pro Asn Pro Phe Tyr Val Glu
            325                 330                 335

Ser Asp Lys Arg Ala Asp Asn Gly Tyr Ser Phe Val Arg Thr Pro Ser
        340                 345                 350

Pro Ala Pro Gly Leu Asp Glu Ser Pro Phe Ile Thr Trp Gly Glu Ile
        355                 360                 365

Asp Gly Thr Pro Met Arg Leu Asp Leu Glu Asp Thr Pro Ile Asp Ile
        370                 375                 380

Gly Gly Ser Ala Asp Gly Pro His Tyr Asn Ile Pro Ser Ala Pro Pro
385                 390                 395                 400

Arg Asp Val Arg Ala His Ser Leu Ser Arg Asp Ala Ser Arg Lys Leu
                405                 410                 415

Arg Glu Arg Ser Asn Ser Met Phe Lys Lys Pro Pro Leu Pro Ser Pro
            420                 425                 430

His Arg Ser Gly Ser Ala Ser Pro Asn Val Arg Thr Leu Ser Pro Ala
        435                 440                 445

Ala Gln Lys Phe Phe Arg Lys Ala Ile Ala Lys Ser Ser Ser Thr Val
    450                 455                 460

Asp Glu Ser Leu Arg Ala Ser Tyr Arg Gly Ala Ser Pro Arg Gly Ala
465                 470                 475                 480

Ser Pro Gly Ala Val Thr Pro Lys Ser Val Arg Ser Ile Ser Arg Phe
                485                 490                 495

Gly Lys Asp Gly Thr Ser Ser Glu Thr Arg Ser Pro
            500                 505

<210> SEQ ID NO 3
<211> LENGTH: 1431
<212> TYPE: DNA
<213> ORGANISM: Homo sapiens

<400> SEQUENCE: 3

| | | |
|---|---|---|
| atggagacgc cgggcgcatc agcgtcgtcc ttgttgcttc ccgccgcgtc caggccccccg | | 60 |
| aggaagcgcg aggcgggaga ggctggggct gcgacgagca agcagcgggt cctggacgag | | 120 |
| gaagagtata tcgagggcct ccagacggtc atccaaaggg atttctttcc tgatgtggag | | 180 |
| aagctccagg cacagaagga gtacctggaa gccgaggaga tggagacttg gaacggatg | | 240 |
| cgccagattg ccatcaagtt tggctctgcc ttgggcaaga tgtcccggga gccccccgcca | | 300 |
| ccctatgtga ctccagccac atttgaaacc cctgaggtgc atgcaggcac tggagtggtg | | 360 |
| ggcaacaagc ccaggccccg cggccgaggc ctggaggatg agaggctgg agaggaggag | | 420 |
| gagaaggagc cgctgcccag cctagatgtc ttcctgagcc gctacacgag tgaggacaat | | 480 |
| gcctccttcc aggagatcat ggaggtggcc aaggagagaa gccgggcacg ccacgcttgg | | 540 |
| ctctaccagg ctgaggaaga gtttgagaag aggcagaaag ataatctcga actcccgtca | | 600 |
| gcagagcacc aggccatcga gagcagccag gccagtgtgg agacctggaa gtacaaggcc | | 660 |
| aagaattccc tcatgtacta tccagagggt gtccctgacg aggagcagct gtttaagaag | | 720 |
| ccccggcagg tggtacataa gaacacgcgc ttccttaggg accccttcag ccaagccctg | | 780 |
| agcaggtgcc agctccagca ggcagccgcc tcaatgccc agcacaaaca gggcaaggtg | | 840 |
| ggccccgatg gcaaggagct gatcccccag gagtcccctc gagtgggtgg atttggattt | | 900 |
| gttgccactc cttcccctgc ccctggtgtg aacgagtccc cgatgatgac ctgggggggag | | 960 |
| gttgagaaca caccccttgag agttgaaggg tcggaaacgc cctacgtgga caggacaccc | | 1020 |
| ggcccagctt ttaagatcct ggagccaggc cgcagggagc ggctgggtct gaagatggcc | | 1080 |

```
aacgaggccg ctgccaagaa ccgggccaag aagcaggaag ccttgcggag agtgacggag    1140
aatctggcca gcctcacccc caaaggcctg agcccagcca tgtcgccagc cctacagcgc    1200
cttgtgagca ggacggccag caagtacaca gaccgggccc tgcgggccag ctacacacca    1260
tccccagcac gctccaccca cctcaagacc ccggccagtg ggctgcagac ccccacaagc    1320
acaccggcgc ctggctctgc cacacgcacc cctctcacac aggacccggc ctccatcacg    1380
gacaacctgc tgcagctccc tgcccggcgc aaagcttcgg acttcttttta g            1431
```

<210> SEQ ID NO 4
<211> LENGTH: 476
<212> TYPE: PRT
<213> ORGANISM: Homo sapiens

<400> SEQUENCE: 4

```
Met Glu Thr Pro Gly Ala Ser Ala Ser Ser Leu Leu Leu Pro Ala Ala
1               5                   10                  15

Ser Arg Pro Pro Arg Lys Arg Glu Ala Gly Glu Ala Gly Ala Ala Thr
            20                  25                  30

Ser Lys Gln Arg Val Leu Asp Glu Glu Tyr Ile Glu Gly Leu Gln
        35                  40                  45

Thr Val Ile Gln Arg Asp Phe Phe Pro Asp Val Glu Lys Leu Gln Ala
50                  55                  60

Gln Lys Glu Tyr Leu Glu Ala Glu Asn Gly Asp Leu Glu Arg Met
65                  70                  75                  80

Arg Gln Ile Ala Ile Lys Phe Gly Ser Ala Leu Gly Lys Met Ser Arg
                85                  90                  95

Glu Pro Pro Pro Tyr Val Thr Pro Ala Thr Phe Glu Thr Pro Glu
            100                 105                 110

Val His Ala Gly Thr Gly Val Gly Asn Lys Pro Arg Pro Arg Gly
        115                 120                 125

Arg Gly Leu Glu Asp Gly Glu Ala Gly Glu Glu Glu Lys Glu Pro
    130                 135                 140

Leu Pro Ser Leu Asp Val Phe Leu Ser Arg Tyr Thr Ser Glu Asp Asn
145                 150                 155                 160

Ala Ser Phe Gln Glu Ile Met Glu Val Ala Lys Glu Arg Ser Arg Ala
                165                 170                 175

Arg His Ala Trp Leu Tyr Gln Ala Glu Glu Phe Glu Lys Arg Gln
            180                 185                 190

Lys Asp Asn Leu Glu Leu Pro Ser Ala Glu His Gln Ala Ile Glu Ser
        195                 200                 205

Ser Gln Ala Ser Val Glu Thr Trp Lys Tyr Lys Ala Lys Asn Ser Leu
    210                 215                 220

Met Tyr Tyr Pro Glu Gly Val Pro Asp Glu Glu Gln Leu Phe Lys Lys
225                 230                 235                 240

Pro Arg Gln Val Val His Lys Asn Thr Arg Phe Leu Arg Asp Pro Phe
                245                 250                 255

Ser Gln Ala Leu Ser Arg Cys Gln Leu Gln Gln Ala Ala Leu Asn
            260                 265                 270

Ala Gln His Lys Gln Gly Lys Val Gly Pro Asp Gly Lys Glu Leu Ile
        275                 280                 285

Pro Gln Glu Ser Pro Arg Val Gly Gly Phe Gly Phe Val Ala Thr Pro
    290                 295                 300

Ser Pro Ala Pro Gly Val Asn Glu Ser Pro Met Met Thr Trp Gly Glu
```

```
            305                 310                 315                 320
Val Glu Asn Thr Pro Leu Arg Val Glu Gly Ser Glu Thr Pro Tyr Val
                    325                 330                 335

Asp Arg Thr Pro Gly Pro Ala Phe Lys Ile Leu Glu Pro Gly Arg Arg
                340                 345                 350

Glu Arg Leu Gly Leu Lys Met Ala Asn Glu Ala Ala Lys Asn Arg
            355                 360                 365

Ala Lys Lys Gln Glu Ala Leu Arg Arg Val Thr Glu Asn Leu Ala Ser
        370                 375                 380

Leu Thr Pro Lys Gly Leu Ser Pro Ala Met Ser Pro Ala Leu Gln Arg
385                 390                 395                 400

Leu Val Ser Arg Thr Ala Ser Lys Tyr Thr Asp Arg Ala Leu Arg Ala
                405                 410                 415

Ser Tyr Thr Pro Ser Pro Ala Arg Ser Thr His Leu Lys Thr Pro Ala
                420                 425                 430

Ser Gly Leu Gln Thr Pro Thr Ser Thr Pro Ala Pro Gly Ser Ala Thr
            435                 440                 445

Arg Thr Pro Leu Thr Gln Asp Pro Ala Ser Ile Thr Asp Asn Leu Leu
        450                 455                 460

Gln Leu Pro Ala Arg Arg Lys Ala Ser Asp Phe Phe
465                 470                 475
```

<210> SEQ ID NO 5
<211> LENGTH: 1431
<212> TYPE: DNA
<213> ORGANISM: Macaca mulatta

<400> SEQUENCE: 5

```
atggagactc cgggcgcatc agcttcgtcc ttgttgctcc ccgccgcgtc caggccccg      60
aggaagcgcg aggcgggaga ggctggggct gcgacgagca agcagcgggt cctggacgag    120
gaagagtata ttgagggcct ccagacagtc atccaaaggg atttctttcc tgatgtggag    180
aagctccagg cacagaagga gtacctggaa gccgaggaga tggagacttg gaacggatg     240
cgccagattg ccatcaaatt tggctctgcc ttgggcaaga tgtcccggga gccccgcca    300
ccctacgtga ctccagccac gttgaaacc cctgaggtgc acgcgggcac tggagtggtg     360
ggcaataagc caggccccg cggccgaggc cggaggatg agaggctgg agaggaggag       420
gagaaggagc cactgcccag cctagatgtc ttcctgagcc gctacacgag tgaggacaat    480
gcctccttcc aggagatcat ggaggtggcc aaggagagga gccgggcacg ccacgcttgg    540
ctctaccagg ctgaggagga gtttgagaag aggcagaaag ataatcttga actcccgtca    600
gcagagcacc aggccatcga gagcagccag gccggtgtgg agacctggaa gtacaaggcc    660
aagaattccc tcatgtacta tccagagggt gtccctgatg aggagcagct gtttaagaag    720
ccccggcagg tggtgcataa gaacacgcgc ttccttaggg atcccttcag ccaagccctg    780
agcaggtgcc agctccagca ggcagccgcc ctcaatgccc agcacaaaca gggcaaggtg    840
ggccctgatg gcaaggagct gatccccag gagtcccctc gagtgggtgg atttggattt     900
gttgccactc cttctcctgc ccctggtgtg aacgagtccc caatgatgac tggggggag     960
gttgagaaca caccgttgag agttgaaggg tcggaaaccc cctacgtgga caggacaccg   1020
ggcccagctt tcaagatcct ggagccgggc cgcagggagc ggctggggct gaagatggcc   1080
aacgaggctg ccgccaagaa ccgggccaag aagcaggaag ccttgcggag agtgacggag   1140
aatctggcca gcctcactcc caaaggcctg aacccagcca tgtccccagc cctacagcgc   1200
```

```
ctcgtgagca ggacggccag caagtacaca gaccgagccc tgcgggccag ctacacacca    1260
tccccagcac gctccaccca cctcaagacc ccggccagtg ggctacagac ccccacaagc    1320
acaccagcgc ctggctctgc cacacgcacc cctctcacgc aggacccggc ctccatcacg    1380
gacaacctgc tgcagctccc tgcccggcgc aaagcctcgg acttcttta g              1431
```

<210> SEQ ID NO 6
<211> LENGTH: 476
<212> TYPE: PRT
<213> ORGANISM: Macaca mulatta

<400> SEQUENCE: 6

```
Met Glu Thr Pro Gly Ala Ser Ala Ser Ser Leu Leu Leu Pro Ala Ala
1               5                   10                  15

Ser Arg Pro Pro Arg Lys Arg Glu Ala Gly Glu Ala Gly Ala Ala Thr
            20                  25                  30

Ser Lys Gln Arg Val Leu Asp Glu Glu Tyr Ile Glu Gly Leu Gln
        35                  40                  45

Thr Val Ile Gln Arg Asp Phe Phe Pro Asp Val Glu Lys Leu Gln Ala
    50                  55                  60

Gln Lys Glu Tyr Leu Glu Ala Glu Asn Gly Asp Leu Glu Arg Met
65                  70                  75                  80

Arg Gln Ile Ala Ile Lys Phe Gly Ser Ala Leu Gly Lys Met Ser Arg
                85                  90                  95

Glu Pro Pro Pro Tyr Val Thr Pro Ala Thr Phe Glu Thr Pro Glu
            100                 105                 110

Val His Ala Gly Thr Gly Val Val Gly Asn Lys Pro Arg Pro Arg Gly
        115                 120                 125

Arg Gly Pro Glu Asp Gly Glu Ala Gly Glu Glu Glu Lys Glu Pro
    130                 135                 140

Leu Pro Ser Leu Asp Val Phe Leu Ser Arg Tyr Thr Ser Glu Asp Asn
145                 150                 155                 160

Ala Ser Phe Gln Glu Ile Met Glu Val Ala Lys Glu Arg Ser Arg Ala
                165                 170                 175

Arg His Ala Trp Leu Tyr Gln Ala Glu Glu Phe Glu Lys Arg Gln
            180                 185                 190

Lys Asp Asn Leu Glu Leu Pro Ser Ala Glu His Gln Ala Ile Glu Ser
        195                 200                 205

Ser Gln Ala Gly Val Glu Thr Trp Lys Tyr Lys Ala Lys Asn Ser Leu
    210                 215                 220

Met Tyr Tyr Pro Glu Gly Val Pro Asp Glu Glu Gln Leu Phe Lys Lys
225                 230                 235                 240

Pro Arg Gln Val Val His Lys Asn Thr Arg Phe Leu Arg Asp Pro Phe
                245                 250                 255

Ser Gln Ala Leu Ser Arg Cys Gln Leu Gln Gln Ala Ala Ala Leu Asn
            260                 265                 270

Ala Gln His Lys Gln Gly Lys Val Gly Pro Asp Gly Lys Glu Leu Ile
        275                 280                 285

Pro Gln Glu Ser Pro Arg Val Gly Gly Phe Gly Phe Val Ala Thr Pro
    290                 295                 300

Ser Pro Ala Pro Gly Val Asn Glu Ser Pro Met Met Thr Trp Gly Glu
305                 310                 315                 320

Val Glu Asn Thr Pro Leu Arg Val Glu Gly Ser Glu Thr Pro Tyr Val
                325                 330                 335
```

Asp Arg Thr Pro Gly Pro Ala Phe Lys Ile Leu Glu Pro Gly Arg Arg
              340                 345                 350

Glu Arg Leu Gly Leu Lys Met Ala Asn Glu Ala Ala Ala Lys Asn Arg
          355                 360                 365

Ala Lys Lys Gln Glu Ala Leu Arg Arg Val Thr Glu Asn Leu Ala Ser
    370                 375                 380

Leu Thr Pro Lys Gly Leu Asn Pro Ala Met Ser Pro Ala Leu Gln Arg
385                 390                 395                 400

Leu Val Ser Arg Thr Ala Ser Lys Tyr Thr Asp Arg Ala Leu Arg Ala
                405                 410                 415

Ser Tyr Thr Pro Ser Pro Ala Arg Ser Thr His Leu Lys Thr Pro Ala
            420                 425                 430

Ser Gly Leu Gln Thr Pro Thr Ser Thr Pro Ala Pro Gly Ser Ala Thr
        435                 440                 445

Arg Thr Pro Leu Thr Gln Asp Pro Ala Ser Ile Thr Asp Asn Leu Leu
    450                 455                 460

Gln Leu Pro Ala Arg Arg Lys Ala Ser Asp Phe Phe
465                 470                 475

<210> SEQ ID NO 7
<211> LENGTH: 1437
<212> TYPE: DNA
<213> ORGANISM: Canis lupus familiaris

<400> SEQUENCE: 7

| | | | | | |
|---|---|---|---|---|---|
| atggagacgc | ctggagcgtc | aaccccggcg | ctattgcttc | ctccctcgtc | cgggccccgg | 60 |
| aggaagcggg | cagcagggga | ggcccgggct | gcggcgagca | agcaacgggt | cctggacgaa | 120 |
| gaagagtaca | tcgagggtct | ccagacagtc | atccaaaggg | acttctttcc | tgacgtggag | 180 |
| aagttgcagg | ctcagaagga | gtacctggag | gctgaggaga | atggagacct | ggaacggatg | 240 |
| cggcagatcg | ccatcaagtt | tggctctgcc | ctgggcaaga | tgtcccggga | gccccacca | 300 |
| ccctatgtga | ctccagccac | atttgaaacc | ctgatgtgc | acacaggcac | ggagtggtg | 360 |
| ggcaacaagc | ctcggggccg | aggcaggggc | ctggaggatg | gcgatggaga | ggctggagag | 420 |
| gaggaggaga | aggagcctct | gcccagcctg | gatgtcttcc | tgagccggta | cacaagtgag | 480 |
| gacaacgcct | ccttccagga | gatcatggag | gtggcgaagg | agaagagccg | ggcacgccac | 540 |
| acgtggctct | accaggccga | ggaggagttt | gagaagaggc | agaaagataa | tcttgcactt | 600 |
| ccgtcggcag | agcaccaagc | catcgagagc | agccaggctg | gcgtggagac | ctggaagtac | 660 |
| aaggccaaaa | actccctcat | gtactaccca | gagggcgtcc | cagatgagga | acagctgttt | 720 |
| aagaagccga | ggcaggtggt | gcataagaat | actcgcttcc | tcagggatcc | cttcagccag | 780 |
| gccctgagca | gatcccagct | gcagcaggct | gccgctctca | acgcccagca | caaacagggc | 840 |
| aaggtgggcc | ctgatggcaa | ggagctaatc | ccccaggact | ccccacgagt | aggcggattt | 900 |
| ggatttgttg | caacaccctc | tcctgcccct | ggtgtgaatg | agtcaccgct | gatgacctgg | 960 |
| ggagaagttg | aaaacactcc | cttgagagtt | gaaggatctg | aaaccccta | cgtggacagg | 1020 |
| acgccaggac | cagccttcaa | gatcttggag | cctggccgca | gggaacggct | ggggctgaag | 1080 |
| atggccaacg | aggctgccgc | caagaaccgg | gccaagaagc | aggaggcctt | gagaagagtg | 1140 |
| acggagaact | tggccagcct | cacccccaaa | ggcctgagcc | cagccatgtc | ccagccctg | 1200 |
| cagcgcctcg | tgagcaggac | ggccagcaag | tacacagacc | gggccctgcg | ggccagctac | 1260 |
| acccccatctc | cagcacgttc | aacccacctc | aagaccccag | ccggtgggcc | tcagacccc | 1320 |

```
acgagcacac cagctcctgg ctctgcggcg cgcacccccc tcagccagga ccccgcctcc   1380
atcacggaca acctgctgca gctccctgcc cggcgcaaag cctcagactt cttctag      1437

<210> SEQ ID NO 8
<211> LENGTH: 478
<212> TYPE: PRT
<213> ORGANISM: Canis lupus familiaris

<400> SEQUENCE: 8

Met Glu Thr Pro Gly Ala Ser Thr Pro Ala Leu Leu Leu Pro Pro Ser
1               5                   10                  15

Ser Gly Pro Arg Arg Lys Arg Ala Ala Gly Glu Ala Arg Ala Ala Ala
            20                  25                  30

Ser Lys Gln Arg Val Leu Asp Glu Glu Tyr Ile Glu Gly Leu Gln
        35                  40                  45

Thr Val Ile Gln Arg Asp Phe Phe Pro Asp Val Glu Lys Leu Gln Ala
    50                  55                  60

Gln Lys Glu Tyr Leu Glu Ala Glu Asn Gly Asp Leu Glu Arg Met
65                  70                  75                  80

Arg Gln Ile Ala Ile Lys Phe Gly Ser Ala Leu Gly Lys Met Ser Arg
                85                  90                  95

Glu Pro Pro Pro Tyr Val Thr Pro Ala Thr Phe Glu Thr Pro Asp
            100                 105                 110

Val His Thr Gly Thr Gly Val Val Gly Asn Lys Pro Arg Gly Arg Gly
        115                 120                 125

Arg Gly Leu Glu Asp Gly Asp Gly Glu Ala Gly Glu Glu Glu Lys
    130                 135                 140

Glu Pro Leu Pro Ser Leu Asp Val Phe Leu Ser Arg Tyr Thr Ser Glu
145                 150                 155                 160

Asp Asn Ala Ser Phe Gln Glu Ile Met Glu Val Ala Lys Glu Lys Ser
                165                 170                 175

Arg Ala Arg His Thr Trp Leu Tyr Gln Ala Glu Glu Phe Glu Lys
            180                 185                 190

Arg Gln Lys Asp Asn Leu Ala Leu Pro Ser Ala Glu His Gln Ala Ile
        195                 200                 205

Glu Ser Ser Gln Ala Gly Val Glu Thr Trp Lys Tyr Lys Ala Lys Asn
    210                 215                 220

Ser Leu Met Tyr Tyr Pro Glu Gly Val Pro Asp Glu Glu Gln Leu Phe
225                 230                 235                 240

Lys Lys Pro Arg Gln Val Val His Lys Asn Thr Arg Phe Leu Arg Asp
                245                 250                 255

Pro Phe Ser Gln Ala Leu Ser Arg Ser Gln Leu Gln Gln Ala Ala Ala
            260                 265                 270

Leu Asn Ala Gln His Lys Gln Gly Lys Val Gly Pro Asp Gly Lys Glu
        275                 280                 285

Leu Ile Pro Gln Asp Ser Pro Arg Val Gly Gly Phe Gly Phe Val Ala
    290                 295                 300

Thr Pro Ser Pro Ala Pro Gly Val Asn Glu Ser Pro Leu Met Thr Trp
305                 310                 315                 320

Gly Glu Val Glu Asn Thr Pro Leu Arg Val Glu Gly Ser Glu Thr Pro
                325                 330                 335

Tyr Val Asp Arg Thr Pro Gly Pro Ala Phe Lys Ile Leu Glu Pro Gly
            340                 345                 350
```

```
Arg Arg Glu Arg Leu Gly Leu Lys Met Ala Asn Glu Ala Ala Ala Lys
            355                 360                 365

Asn Arg Ala Lys Lys Gln Glu Ala Leu Arg Arg Val Thr Glu Asn Leu
        370                 375                 380

Ala Ser Leu Thr Pro Lys Gly Leu Ser Pro Ala Met Ser Pro Ala Leu
385                 390                 395                 400

Gln Arg Leu Val Ser Arg Thr Ala Ser Lys Tyr Thr Asp Arg Ala Leu
                405                 410                 415

Arg Ala Ser Tyr Thr Pro Ser Pro Ala Arg Ser Thr His Leu Lys Thr
                420                 425                 430

Pro Ala Gly Gly Pro Gln Thr Pro Thr Ser Thr Pro Ala Pro Gly Ser
            435                 440                 445

Ala Ala Arg Thr Pro Leu Ser Gln Asp Pro Ala Ser Ile Thr Asp Asn
    450                 455                 460

Leu Leu Gln Leu Pro Ala Arg Arg Lys Ala Ser Asp Phe Phe
465                 470                 475
```

```
<210> SEQ ID NO 9
<211> LENGTH: 1434
<212> TYPE: DNA
<213> ORGANISM: Felis catus

<400> SEQUENCE: 9
atggagacgc ccggcgcatc aacccgggcc ctgctgctcc ctgccgcgtc cgggccccgg      60
aggaagcgcg cggcagggga gtcgcttgcg acgagcaagc aacgggtcct ggacgaagaa     120
gagtacatcg agggcctcca gacagtcatc cagagggact tctttcctga tgtagaaaag     180
ctgcaggccc agaaagagta cctggaggct gaggagaatg agacctggag cggatgcgt     240
cagattgcca tcaagtttgg ctctgccctg ggcaagatgt cccgagagcc ccaccgccc     300
tatgtgactc cagccacatt tgaaacccct gatgtgcaca caggcaccgg aatggtgggc     360
aacaagcccc gggccggggg ccgaggcctg aagatggcg atggagaggc tggagaggag     420
gaggagaagg agccctgcc cagcctggat gtcttcctga ccggtatac aagtgaggac     480
aatgcctcct tccaggagat catggaggtg gccaaggaga gagccgggc acgccacaca     540
tggctatacc aggccgagga ggagtttgag aagaggcaga agataatct tgcacttccg     600
tcggcagagc accaagccat cgagagcagc caggccggtg tggagacctg aagtacaag     660
gccaaaaact ccctgatgta ctacccagag ggtgtccctg atgaagaaca gctgtttaag     720
aagccaaggc aggtggtgca taagaatact cgcttcctca gggaccccctt cagccaggcc    780
ctgagcaggt cccagctgca gcaggccgcc gccctcaatg cccagcacaa acagggcaag    840
gtgggccctg atggcaaaga actgatcccc caggattccc ccgagtgggg cggatttgga    900
tttgttgcaa cccctctcc tgcccctggt gtgaacgagt caccgctgat gacctggggg    960
gaggttgaaa acactccctt gcgagtggaa ggatctgaga cccctatgt ggacaggaca   1020
ccagggccag ccttcaagat cttggagccg gccgcaggg aacggctggg gctgaagatg    1080
gccaacgagg ctgcagccaa gaaccgggcc aagaagcagg aagccttgag agagtgacg    1140
gagaacctgg ccagcctcac ccccaaaggc ctgagcccag ccatgtctcc agccctgcag    1200
cgcctcgtga gcaggacggc cagcaagtac acagaccggg ccctgcgggc cagctacacc    1260
ccatctccag cacgctcaac ccacctcaag accccagctg gtgggcccca gaccccacg    1320
agcacgccgc ctcctggctc tacagcacgc accccctca accaagatcc agcctccatc    1380
acggacaatc tgctacaact ccctgcccgg cgcaaagcct cagacttctt ctag          1434
```

<210> SEQ ID NO 10
<211> LENGTH: 477
<212> TYPE: PRT
<213> ORGANISM: Felis catus

<400> SEQUENCE: 10

Met Glu Thr Pro Gly Ala Ser Thr Arg Ala Leu Leu Pro Ala Ala
1               5                   10                  15

Ser Gly Pro Arg Arg Lys Arg Ala Ala Gly Glu Ser Leu Ala Thr Ser
                20                  25                  30

Lys Gln Arg Val Leu Asp Glu Glu Tyr Ile Glu Gly Leu Gln Thr
            35                  40                  45

Val Ile Gln Arg Asp Phe Phe Pro Asp Val Glu Lys Leu Gln Ala Gln
        50                  55                  60

Lys Glu Tyr Leu Glu Ala Glu Asn Gly Asp Leu Glu Arg Met Arg
65                  70                  75                  80

Gln Ile Ala Ile Lys Phe Gly Ser Ala Leu Gly Lys Met Ser Arg Glu
                85                  90                  95

Pro Pro Pro Pro Tyr Val Thr Pro Ala Thr Phe Glu Thr Pro Asp Val
                100                 105                 110

His Thr Gly Thr Gly Met Val Gly Asn Lys Pro Arg Gly Arg Gly Arg
            115                 120                 125

Gly Leu Glu Asp Gly Asp Gly Glu Ala Gly Glu Glu Glu Lys Glu
        130                 135                 140

Pro Leu Pro Ser Leu Asp Val Phe Leu Ser Arg Tyr Thr Ser Glu Asp
145                 150                 155                 160

Asn Ala Ser Phe Gln Glu Ile Met Glu Val Ala Lys Glu Lys Ser Arg
                165                 170                 175

Ala Arg His Thr Trp Leu Tyr Gln Ala Glu Glu Phe Glu Lys Arg
            180                 185                 190

Gln Lys Asp Asn Leu Ala Leu Pro Ser Ala Glu His Gln Ala Ile Glu
        195                 200                 205

Ser Ser Gln Ala Gly Val Glu Thr Trp Lys Tyr Lys Ala Lys Asn Ser
210                 215                 220

Leu Met Tyr Tyr Pro Glu Gly Val Pro Asp Glu Gln Leu Phe Lys
225                 230                 235                 240

Lys Pro Arg Gln Val Val His Lys Asn Thr Arg Phe Leu Arg Asp Pro
                245                 250                 255

Phe Ser Gln Ala Leu Ser Arg Ser Gln Leu Gln Gln Ala Ala Ala Leu
            260                 265                 270

Asn Ala Gln His Lys Gln Gly Lys Val Gly Pro Asp Gly Lys Glu Leu
        275                 280                 285

Ile Pro Gln Asp Ser Pro Arg Val Gly Gly Phe Gly Phe Val Ala Thr
        290                 295                 300

Pro Ser Pro Ala Pro Gly Val Asn Glu Ser Pro Leu Met Thr Trp Gly
305                 310                 315                 320

Glu Val Glu Asn Thr Pro Leu Arg Val Glu Gly Ser Glu Thr Pro Tyr
                325                 330                 335

Val Asp Arg Thr Pro Gly Pro Ala Phe Lys Ile Leu Glu Pro Gly Arg
            340                 345                 350

Arg Glu Arg Leu Gly Leu Lys Met Ala Asn Glu Ala Ala Ala Lys Asn
        355                 360                 365

Arg Ala Lys Lys Gln Glu Ala Leu Arg Arg Val Thr Glu Asn Leu Ala

```
                370              375              380
Ser Leu Thr Pro Lys Gly Leu Ser Pro Ala Met Ser Pro Ala Leu Gln
385                  390                  395                 400

Arg Leu Val Ser Arg Thr Ala Ser Lys Tyr Thr Asp Arg Ala Leu Arg
                405                  410                  415

Ala Ser Tyr Thr Pro Ser Pro Ala Arg Ser Thr His Leu Lys Thr Pro
            420                  425                  430

Ala Gly Gly Pro Gln Thr Pro Thr Ser Thr Pro Ala Pro Gly Ser Thr
        435                  440                  445

Ala Arg Thr Pro Leu Asn Gln Asp Pro Ala Ser Ile Thr Asp Asn Leu
    450                  455                  460

Leu Gln Leu Pro Ala Arg Arg Lys Ala Ser Asp Phe Phe
465                  470                  475

<210> SEQ ID NO 11
<211> LENGTH: 1449
<212> TYPE: DNA
<213> ORGANISM: Myotis lucifugus

<400> SEQUENCE: 11
atggagacgc ccagagcgtc tccccgggcc ctgctgcttt ccaccgcgtc cgggcccggg     60
agaaagcggg cggctgggga ggccgggggt gtgacgagga agcaaaaggt cttggacgag    120
gaagagtaca tcgagggcct ccagacagtc atccagaggg acttctttcc tgacgtggag    180
aagctgcagg cacagaagga atatctggag gccgaggaga tggagacct ggaacggatg     240 cgccagattg ccatcaagtt tggctctgct ctgggcaaga tgtcccgaga gcccccgccg    300
ccctatgtga ctccagccac gtttgaaacc ctgaggtgc acacagggac tggagtggtg     360
ggccagaagc ccagggccg aggccagggc ctggaggatg gtgatggaga ggctggagag     420
gaggaggaga aggagcccct gcccagcctg gatgtcttcc tgagccggta cacaagcgag    480
gacaacgcct ccttccagga gatcatggag gtggccaagg agaagagccg ggcacgccat    540
gcctggctct accaggccga ggaggagttt gagaagaggc agaaagataa tcttgccctc    600
ccgtcggcag agcaccaagc cattgagagc agccaggccg cgtagagac ctggaaatac     660 aaggccaaga attccctcat gtactaccca gagggcgtcc ctgatgagga gcagctgttt    720
aagaagcccc ggcaggtggt gcacaagaat actcgcttcc tcaggacccc cttcagccag    780
gccctgagcc aggccctgag caggtctcag ctgcagcagg ctgctgccct caatgcccag    840
cacaaacagg gcaaggtggg ccccgatggc aaggagctga tccccagga tccctcga      900 gtgggcggat ttggatttgt tgccacccct tctcctgccc ctggtgtgaa cgagtctccg    960
ttgatgacct ggggagaggt tgagaacaca ccagtgagag ttgaaggatc agaaaccccc   1020
tacgtggaca ggacaccagg gccagccttc aagatcttag agccgggccg cagggagcgg   1080
ctggggctga agatggccaa cgaggctgct gccaagaacc gggccaagaa gcaggaggcc   1140
ttgcggagag tgacggagaa cctggccagc ctcaccccca aaggcctgag ccccgccatg   1200
tccccagccc tgcagcgcct tgtgagcaga acagccagca agtacacaga ccgggccctg   1260
cgggccagct acacaccgtc cccagcacgc tcagcccacc tcaagacccc ggccggcggg   1320
ccccagaccc cgacgagcac accagctcct ggctcggcca cacgcacccc cctcagccag   1380
gacccggcct ccatcacaga caacctgctg cagctccctg cccggcgcaa agcctcagac   1440
ttcttctag                                                           1449
```

<210> SEQ ID NO 12
<211> LENGTH: 482
<212> TYPE: PRT
<213> ORGANISM: Myotis lucifugus

<400> SEQUENCE: 12

```
Met Glu Thr Pro Arg Ala Ser Pro Arg Ala Leu Leu Leu Ser Thr Ala
1               5                   10                  15

Ser Gly Pro Gly Arg Lys Arg Ala Ala Gly Glu Ala Gly Gly Val Thr
            20                  25                  30

Arg Lys Gln Lys Val Leu Asp Glu Glu Tyr Ile Glu Gly Leu Gln
        35                  40                  45

Thr Val Ile Gln Arg Asp Phe Phe Pro Asp Val Glu Lys Leu Gln Ala
    50                  55                  60

Gln Lys Glu Tyr Leu Glu Ala Glu Glu Asn Gly Asp Leu Glu Arg Met
65                  70                  75                  80

Arg Gln Ile Ala Ile Lys Phe Gly Ser Ala Leu Gly Lys Met Ser Arg
                85                  90                  95

Glu Pro Pro Pro Pro Tyr Val Thr Pro Ala Thr Phe Glu Thr Pro Glu
            100                 105                 110

Val His Thr Gly Thr Gly Val Val Gly Gln Lys Pro Gln Gly Arg Gly
        115                 120                 125

Gln Gly Leu Glu Asp Gly Asp Gly Glu Ala Gly Glu Glu Glu Lys
    130                 135                 140

Glu Pro Leu Pro Ser Leu Asp Val Phe Leu Ser Arg Tyr Thr Ser Glu
145                 150                 155                 160

Asp Asn Ala Ser Phe Gln Glu Ile Met Glu Val Ala Lys Glu Lys Ser
                165                 170                 175

Arg Ala Arg His Ala Trp Leu Tyr Gln Ala Glu Glu Phe Glu Lys
            180                 185                 190

Arg Gln Lys Asp Asn Leu Ala Leu Pro Ser Ala Glu His Gln Ala Ile
    195                 200                 205

Glu Ser Ser Gln Ala Gly Val Glu Thr Trp Lys Tyr Lys Ala Lys Asn
210                 215                 220

Ser Leu Met Tyr Tyr Pro Glu Gly Val Pro Asp Glu Glu Gln Leu Phe
225                 230                 235                 240

Lys Lys Pro Arg Gln Val Val His Lys Asn Thr Arg Phe Leu Arg Asp
                245                 250                 255

Pro Phe Ser Gln Ala Leu Ser Gln Ala Leu Ser Arg Ser Gln Leu Gln
            260                 265                 270

Gln Ala Ala Leu Asn Ala Gln His Lys Gln Gly Lys Val Gly Pro
    275                 280                 285

Asp Gly Lys Glu Leu Ile Pro Gln Glu Ser Pro Arg Val Gly Gly Phe
290                 295                 300

Gly Phe Val Ala Thr Pro Ser Pro Ala Pro Gly Val Asn Glu Ser Pro
305                 310                 315                 320

Leu Met Thr Trp Gly Glu Val Glu Asn Thr Pro Val Arg Val Glu Gly
                325                 330                 335

Ser Glu Thr Pro Tyr Val Asp Arg Thr Pro Gly Pro Ala Phe Lys Ile
            340                 345                 350

Leu Glu Pro Gly Arg Arg Glu Arg Leu Gly Leu Lys Met Ala Asn Glu
    355                 360                 365

Ala Ala Ala Lys Asn Arg Ala Lys Lys Gln Glu Ala Leu Arg Arg Val
370                 375                 380
```

Thr Glu Asn Leu Ala Ser Leu Thr Pro Lys Gly Leu Ser Pro Ala Met
385                 390                 395                 400

Ser Pro Ala Leu Gln Arg Leu Val Ser Arg Thr Ala Ser Lys Tyr Thr
            405                 410                 415

Asp Arg Ala Leu Arg Ala Ser Tyr Thr Pro Ser Pro Ala Arg Ser Ala
        420                 425                 430

His Leu Lys Thr Pro Ala Gly Gly Pro Gln Thr Pro Thr Ser Thr Pro
            435                 440                 445

Ala Pro Gly Ser Ala Thr Arg Thr Pro Leu Ser Gln Asp Pro Ala Ser
    450                 455                 460

Ile Thr Asp Asn Leu Leu Gln Leu Pro Ala Arg Arg Lys Ala Ser Asp
465                 470                 475                 480

Phe Phe

<210> SEQ ID NO 13
<211> LENGTH: 1440
<212> TYPE: DNA
<213> ORGANISM: Mus musculus

<400> SEQUENCE: 13
atggggacgc ccgggacctc ggcgggtgct ctgtttctgt cctccgcgtc cgcgccctca      60
aggaagcgcg cggctgggga ggctggagag gccggagttg cgagaagcag gcagcgggtc     120
ctggatgaag aagagtacat cgagggactt cagacagtta tccagagaga cttcttccct     180
gatgtggaga agctacaggc acagaaggag tacctggagg ccgaggaaaa cggagatttg     240
gagcgcatgc gccagattgc catcaagttt ggctctgccc tgggcaagat atctcgggaa     300
cctccaccac cctatgttac tccagccacc tttgaaactc ctgaggtaca cccaggctct     360
gctgtgctgg caacaagcc ccggcccag ggccgagacc tagatgatgg agaggctgga     420
gaggaagagg agaaggagcc actgcccagc ctggatgtct tcttgagcca gtacacaagt     480
gaggacaatg cctccttcca ggagatcatg gaggtggcca ggaaaaaag ccatgcacgg     540
cacgcgtggc tctaccaggc tgaggaggaa tttgagaagc gacagaaaga taatcttgaa     600
ctcccatcgg cagagcatca agccattgag agcagtcagg ctggagtgga gacctggaag     660
tacaaggcca agaactctct catgtactat cccgagggtg tccctgatga agagcagttg     720
tttaagaagc cgagacagat agtacataag aacacacgtt tcctccgaga tcccttcagt     780
caggctttga gcaggtccca gcttcagcag gcggctgccc tcaatgccca gcacaaacag     840
ggcaaggtcg gccctgacgg caaggaactc attccccagg agtcccccag agtgggcggc     900
tttggatttg ttgccactcc ttctcctgct cctggtgtga atgagtcccc actgatgaca     960
tggggagagg ttgagaacac gcccctgcga gtagaaggat ccgagagccc ctatgtggac    1020
aggacacctg acccacatt caagatcttg gagccaggac gcagggagcg tctgggcctg    1080
aagatggcca atgaagcggc tgccaaaaac cgggcgaaga agcaggaagc gttgcggaga    1140
gttacagaga acttggccag tcttactccc aaaggcttga gccagccat gtccccagcc    1200
ctacagcgcc tcgtaagcag gacagccagc aagtacacag atcgtgccct gcgggccagc    1260
tatacaccat cccagcacg atcttcccac tcaagaccc cagctggtgg gccgcagaca    1320
cccacaagca ctccagcccc tgggtctgct acacgcacac ccctcacaca ggacccagcc    1380
tccatcacag acaacctgct gcagctccct gcccgacgca aagcttcaga cttctttag    1440

<210> SEQ ID NO 14
<211> LENGTH: 479

<212> TYPE: PRT
<213> ORGANISM: Mus musculus

<400> SEQUENCE: 14

```
Met Gly Thr Pro Gly Thr Ser Ala Gly Ala Leu Phe Leu Ser Ser Ala
1               5                   10                  15

Ser Ala Pro Ser Arg Lys Arg Ala Ala Gly Glu Ala Gly Glu Ala Gly
            20                  25                  30

Val Ala Arg Ser Arg Gln Arg Val Leu Asp Glu Glu Glu Tyr Ile Glu
        35                  40                  45

Gly Leu Gln Thr Val Ile Gln Arg Asp Phe Phe Pro Asp Val Glu Lys
    50                  55                  60

Leu Gln Ala Gln Lys Glu Tyr Leu Glu Ala Glu Asn Gly Asp Leu
65                  70                  75                  80

Glu Arg Met Arg Gln Ile Ala Ile Lys Phe Gly Ser Ala Leu Gly Lys
                85                  90                  95

Ile Ser Arg Glu Pro Pro Pro Tyr Val Thr Pro Ala Thr Phe Glu
            100                 105                 110

Thr Pro Glu Val His Pro Gly Ser Ala Val Leu Gly Asn Lys Pro Arg
        115                 120                 125

Pro Gln Gly Arg Asp Leu Asp Gly Glu Ala Gly Glu Glu Glu
130                 135                 140

Lys Glu Pro Leu Pro Ser Leu Asp Val Phe Leu Ser Gln Tyr Thr Ser
145                 150                 155                 160

Glu Asp Asn Ala Ser Phe Gln Glu Ile Met Glu Val Ala Lys Glu Lys
                165                 170                 175

Ser His Ala Arg His Ala Trp Leu Tyr Gln Ala Glu Glu Phe Glu
            180                 185                 190

Lys Arg Gln Lys Asp Asn Leu Glu Leu Pro Ser Ala His Gln Ala
        195                 200                 205

Ile Glu Ser Ser Gln Ala Gly Val Glu Thr Trp Lys Tyr Lys Ala Lys
    210                 215                 220

Asn Ser Leu Met Tyr Tyr Pro Glu Gly Val Pro Asp Glu Glu Gln Leu
225                 230                 235                 240

Phe Lys Lys Pro Arg Gln Ile Val His Lys Asn Thr Arg Phe Leu Arg
                245                 250                 255

Asp Pro Phe Ser Gln Ala Leu Ser Arg Ser Gln Leu Gln Ala Ala
            260                 265                 270

Ala Leu Asn Ala Gln His Lys Gln Gly Lys Val Gly Pro Asp Gly Lys
        275                 280                 285

Glu Leu Ile Pro Gln Glu Ser Pro Arg Val Gly Gly Phe Gly Phe Val
    290                 295                 300

Ala Thr Pro Ser Pro Ala Pro Gly Val Asn Glu Ser Pro Leu Met Thr
305                 310                 315                 320

Trp Gly Glu Val Glu Asn Thr Pro Leu Arg Val Glu Gly Ser Glu Ser
                325                 330                 335

Pro Tyr Val Asp Arg Thr Pro Gly Pro Thr Phe Lys Ile Leu Glu Pro
            340                 345                 350

Gly Arg Arg Glu Arg Leu Gly Leu Lys Met Ala Asn Glu Ala Ala Ala
        355                 360                 365

Lys Asn Arg Ala Lys Lys Gln Glu Ala Leu Arg Val Thr Glu Asn
    370                 375                 380

Leu Ala Ser Leu Thr Pro Lys Gly Leu Ser Pro Ala Met Ser Pro Ala
385                 390                 395                 400
```

Leu Gln Arg Leu Val Ser Arg Thr Ala Ser Lys Tyr Thr Asp Arg Ala
            405                 410                 415

Leu Arg Ala Ser Tyr Thr Pro Ser Pro Ala Arg Ser Ser His Leu Lys
        420                 425                 430

Thr Pro Ala Gly Gly Pro Gln Thr Pro Thr Ser Thr Pro Ala Pro Gly
        435                 440                 445

Ser Ala Thr Arg Thr Pro Leu Thr Gln Asp Pro Ala Ser Ile Thr Asp
    450                 455                 460

Asn Leu Leu Gln Leu Pro Ala Arg Arg Lys Ala Ser Asp Phe Phe
465                 470                 475

```
<210> SEQ ID NO 15
<211> LENGTH: 1545
<212> TYPE: DNA
<213> ORGANISM: Populus trichocarpa

<400> SEQUENCE: 15
atgctactct ctccaggaca ctcaccacgc cacctttcat ctccgtcacc atattcaaat      60
tccgaaaata ccctccagat ctccagcaat tcctcctcga tcaacaacac cccgataaac    120
cctagtaaac accccacagt tcttgacgag acacctatg tggccaccat cgagaaaatc     180
atcgagcgcg acttcttccc tgatatctcg aagctacgtg accgtcttga ttggctcgaa    240
gctatgaaat cgggcgatcc gatccaaatt cgagatgccc agttgaagat tatggagcgc    300
cgtggcaaaa aggtaaacaa tcccagctcc gacggcagct tcggagtag aaatcgaacc     360
caaaccccag gttctacttt tatgcgtagt cttactccat tgatgaatt tgatagcagg     420
attcaaacac ctggcgttgt tatggatagg ggattatcta gtaatgcaga gtctaatgag    480
aatgaagttg ctgttgataa gaatttgagt ttagacgaat tttttaggag atatacgagt    540
gaggataacg atagcttttc aaagatatta gagaaagtga ataggaaaag gaaggagaga    600
tatgagcatt tgttagaagg tgaaaaggag gatgttaaat tcattgggga tgcgaagagg    660
gataggatta cagatggttt tggaacttct gatcagccac cgagcacatt ggaaggatgg    720
aagtacacag cgaagaattt gctgatgtat catccggctg ataggggtga ggctccattg    780
actgaggagg aacaggctgt tagattgaag ggtttgacta agaaaatcaa taggtccagc    840
acacgttttc atggtaagat gttggatact aggccaagag atgatggtgt tgttgaggtg    900
ctttatactc ctgtagctgg ggctactcca cttcctatgt atgatagga cggggataag    960
gcaaagaagt atgatttgga ggatttgagg aggacaccag ataggtttta tgtggaatca   1020
gggaagaagg cagatgatgg gtatagtttt gttaggacac catcaccggc tcctggagtt   1080
gatgagtcgc catttattac ttggggtgag attgaaggga caccaatgag gttggaacct   1140
gaggataccc cgattgatat tggtggtagt ggcaatgggc cgcattttaa aatccctaat   1200
ccacctgcac gggatgtgaa ggcccattca ttgtcgaggg aggcttcgcg aaggttgagg   1260
gagaagtcaa agatgtttca aaagccaccg ctgccctctc caagtagagg ggggagcgct   1320
agtccaagtg tgcggacgct ctctcctgct gcacagaagt ttgtgaggaa tgcaatttcc   1380
aggtcttcat cctctgtaga tgaaaccctc cgtgccagtt atagagggc aagtccagga   1440
gttggtactc ctaagagtgg aaggagtatc tcgaggtttg aagagatgg gagcataagt   1500
tccaggtcac cttctgtaag ggagaattct aatcctcctt ggtaa                   1545

<210> SEQ ID NO 16
<211> LENGTH: 514
```

```
<212> TYPE: PRT
<213> ORGANISM: Populus trichocarpa

<400> SEQUENCE: 16

Met Leu Leu Ser Pro Gly His Ser Pro Arg His Leu Ser Ser Pro Ser
1               5                   10                  15

Pro Tyr Ser Asn Ser Glu Asn Thr Leu Gln Ile Ser Ser Asn Ser Ser
            20                  25                  30

Ser Ile Asn Asn Thr Pro Ile Asn Pro Ser Lys His Pro Thr Val Leu
        35                  40                  45

Asp Glu Asp Thr Tyr Val Ala Thr Ile Glu Lys Ile Ile Glu Arg Asp
    50                  55                  60

Phe Phe Pro Asp Ile Ser Lys Leu Arg Asp Arg Leu Asp Trp Leu Glu
65                  70                  75                  80

Ala Met Lys Ser Gly Asp Pro Ile Gln Ile Arg Asp Ala Gln Leu Lys
                85                  90                  95

Ile Met Glu Arg Arg Gly Lys Lys Val Asn Asn Pro Ser Ser Asp Gly
            100                 105                 110

Ser Phe Arg Ser Arg Asn Arg Thr Gln Thr Pro Gly Ser Thr Phe Met
        115                 120                 125

Arg Ser Leu Thr Pro Phe Asp Glu Phe Asp Ser Arg Ile Gln Thr Pro
    130                 135                 140

Gly Val Val Met Asp Arg Gly Leu Ser Ser Asn Ala Glu Ser Asn Glu
145                 150                 155                 160

Asn Glu Val Ala Val Asp Lys Asn Leu Ser Leu Asp Glu Phe Phe Arg
                165                 170                 175

Arg Tyr Thr Ser Glu Asp Asn Asp Ser Phe Ser Lys Ile Leu Glu Lys
            180                 185                 190

Val Asn Arg Lys Arg Lys Glu Arg Tyr Glu His Leu Leu Glu Gly Glu
        195                 200                 205

Lys Glu Asp Val Lys Phe Ile Gly Asp Ala Lys Arg Asp Arg Ile Thr
    210                 215                 220

Asp Gly Phe Gly Thr Ser Asp Gln Pro Pro Ser Thr Leu Glu Gly Trp
225                 230                 235                 240

Lys Tyr Thr Ala Lys Asn Leu Leu Met Tyr His Pro Ala Asp Arg Gly
                245                 250                 255

Glu Ala Pro Leu Thr Glu Glu Gln Ala Val Arg Leu Lys Gly Leu
            260                 265                 270

Thr Lys Glu Ile Asn Arg Ser Ser Thr Arg Phe His Gly Lys Met Leu
        275                 280                 285

Asp Thr Arg Pro Arg Asp Asp Gly Val Val Glu Val Leu Tyr Thr Pro
    290                 295                 300

Val Ala Gly Ala Thr Pro Leu Pro Met Tyr Asp Arg Asp Gly Asp Lys
305                 310                 315                 320

Ala Lys Lys Tyr Asp Leu Glu Asp Leu Arg Arg Thr Pro Asp Arg Phe
                325                 330                 335

Tyr Val Glu Ser Gly Lys Lys Ala Asp Asp Gly Tyr Ser Phe Val Arg
            340                 345                 350

Thr Pro Ser Pro Ala Pro Gly Val Asp Glu Ser Pro Phe Ile Thr Trp
        355                 360                 365

Gly Glu Ile Glu Gly Thr Pro Met Arg Leu Glu Pro Glu Asp Thr Pro
    370                 375                 380

Ile Asp Ile Gly Gly Ser Gly Asn Gly Pro His Phe Lys Ile Pro Asn
385                 390                 395                 400
```

```
Pro Pro Ala Arg Asp Val Lys Ala His Ser Leu Ser Arg Glu Ala Ser
            405                 410                 415
Arg Arg Leu Arg Glu Lys Ser Lys Met Phe Gln Lys Pro Pro Leu Pro
        420                 425                 430
Ser Pro Ser Arg Gly Gly Ser Ala Ser Pro Ser Val Arg Thr Leu Ser
            435                 440                 445
Pro Ala Ala Gln Lys Phe Val Arg Asn Ala Ile Ser Arg Ser Ser Ser
    450                 455                 460
Ser Val Asp Glu Thr Leu Arg Ala Ser Tyr Arg Gly Ala Ser Pro Gly
465                 470                 475                 480
Val Gly Thr Pro Lys Ser Gly Arg Ser Ile Ser Arg Phe Gly Arg Asp
                485                 490                 495
Gly Ser Ile Ser Ser Arg Ser Pro Ser Val Arg Glu Asn Ser Asn Pro
            500                 505                 510
Pro Trp

<210> SEQ ID NO 17
<211> LENGTH: 1533
<212> TYPE: DNA
<213> ORGANISM: Medicago truncatula

<400> SEQUENCE: 17
atgcttcaat caccaggtca ctctccactc catctctcat caccatcacc ttcaccttca     60
atttctgaat tttcaatcca aaaccctaaa aaatctaatt caagtgttca acaccagaag    120
aatcatcgcc acccaacggt tctcgatgaa gatacatacg ctgaagcttt ggagaagata    180
atcgagcgtg attactttcc tgatatctca aagcttcgtg atcgacttga ttggcttgaa    240
gcgataaaaa ctggtgatcc tgttcaaatt cgtgatgccc agttgaagat tatcgagcgt    300
cgtcgtgttg gcggcggaaa ggtaacacct ttacatactg ttgattctag aatttcgcgg    360
acgccgggtt cgacttttgt tagaaatttt accccttttag atgaatttga tggtaaaacg    420
cctgtagtga atggtttagg ggttggtgag ggtgagaaag aggatgttgg tggtgtggat    480
acgaatcttg gcttgatca gttttgggg aggtatacaa gtgaggataa tcaaagtttt    540
tcgaagattt tggagagagt taataggaag aggaaagaga ggtttggtta tttggaagat    600
agtgtgaatt cgaatgcgaa tggggatgct gttgaggatg aaaagaggga taggataact    660
gatgggtatg gtacttctta tcaacctcct agtacgttgg aaggatggaa ttatacggcg    720
aagaatttgt tgatgtatca tcctgctgat cgggggtgagg ttccattgac tgaggaggaa    780
agggctgtta gaattaaagc tgccacgaag gagattgatc gggtgaatac caggtttcat    840
ggtaaaatga tggattctag gccgaaagag gatggaacag ttgagatgct ttatactcct    900
gttgccggtg ctactccggt gcctatgtct tttagagatg cggataagtt gaagaagtat    960
gatttggagg atttgaggaa gactccgaat ccgttttatt tggaatctgg gaagaaagct   1020
gataatggtt atagctatgt taagacgcca tctcctgcac cggagctgaa tgagtctccg   1080
tttattactt ggggagaaat tgaagggact ccgctgaggt tggatatgga ggatacgccg   1140
attgatattg gtggtagtgc tgatggacct cattatagga ttccttctgc accggctaga   1200
gatgccaagg cacactcgct ttctagggag gctgcgcgga atttgaggga gaggtcgaag   1260
aagttctgta aaccccctt ggcatcacca gctagaggtg aagtgctag tccaagcatg   1320 cggacgcttt ctcctgcagc tcagaagttc gttcggaatg caattgcaaa gtcatcgtct   1380
tctgttgacg agacactccg tgcaagttac cgtggttcta ctcctgcttt ggctactcct   1440
```

-continued

```
acaagagtta gaagtgtgtc gaggcttggt cgagacgaga gcacagtttc caggtctcca    1500
tctgttagag acggctccaa tcctccctgg tga                                  1533
```

<210> SEQ ID NO 18
<211> LENGTH: 510
<212> TYPE: PRT
<213> ORGANISM: Medicago truncatula

<400> SEQUENCE: 18

```
Met Leu Gln Ser Pro Gly His Ser Pro Leu His Leu Ser Pro Ser
1               5                   10                  15

Pro Ser Pro Ser Ile Ser Glu Phe Ser Ile Gln Asn Pro Lys Lys Ser
                20                  25                  30

Asn Ser Ser Val Gln His Gln Lys Asn His Arg His Pro Thr Val Leu
            35                  40                  45

Asp Glu Asp Thr Tyr Ala Glu Ala Leu Glu Lys Ile Ile Glu Arg Asp
        50                  55                  60

Tyr Phe Pro Asp Ile Ser Lys Leu Arg Asp Arg Leu Asp Trp Leu Glu
65                  70                  75                  80

Ala Ile Lys Thr Gly Asp Pro Val Gln Ile Arg Asp Ala Gln Leu Lys
                85                  90                  95

Ile Ile Glu Arg Arg Arg Val Gly Gly Lys Val Thr Pro Leu His
            100                 105                 110

Thr Val Asp Ser Arg Ile Ser Arg Thr Pro Gly Ser Thr Phe Val Arg
        115                 120                 125

Asn Phe Thr Pro Leu Asp Glu Phe Asp Gly Lys Thr Pro Val Val Asn
130                 135                 140

Gly Leu Gly Val Gly Glu Gly Glu Lys Glu Asp Val Gly Gly Val Asp
145                 150                 155                 160

Thr Asn Leu Gly Leu Asp Gln Phe Leu Gly Arg Tyr Thr Ser Glu Asp
                165                 170                 175

Asn Gln Ser Phe Ser Lys Ile Leu Glu Arg Val Asn Arg Lys Arg Lys
            180                 185                 190

Glu Arg Phe Gly Tyr Leu Glu Asp Ser Val Asn Ser Asn Ala Asn Gly
        195                 200                 205

Asp Ala Val Glu Asp Glu Lys Arg Asp Arg Ile Thr Asp Gly Tyr Gly
    210                 215                 220

Thr Ser Tyr Gln Pro Pro Ser Thr Leu Glu Gly Trp Asn Tyr Thr Ala
225                 230                 235                 240

Lys Asn Leu Leu Met Tyr His Pro Ala Asp Arg Gly Glu Val Pro Leu
                245                 250                 255

Thr Glu Glu Arg Ala Val Arg Ile Lys Ala Ala Thr Lys Glu Ile
            260                 265                 270

Asp Arg Val Asn Thr Arg Phe His Gly Lys Met Met Asp Ser Arg Pro
        275                 280                 285

Lys Glu Asp Gly Thr Val Glu Met Leu Tyr Thr Pro Val Ala Gly Ala
    290                 295                 300

Thr Pro Val Pro Met Ser Phe Arg Asp Ala Asp Lys Leu Lys Lys Tyr
305                 310                 315                 320

Asp Leu Glu Asp Leu Arg Lys Thr Pro Asn Pro Phe Tyr Leu Glu Ser
                325                 330                 335

Gly Lys Lys Ala Asp Asn Gly Tyr Ser Tyr Val Lys Thr Pro Ser Pro
            340                 345                 350
```

-continued

```
Ala Pro Gly Ala Asp Glu Ser Pro Phe Ile Thr Trp Gly Glu Ile Glu
            355                 360                 365

Gly Thr Pro Leu Arg Leu Asp Met Glu Asp Thr Pro Ile Asp Ile Gly
        370                 375                 380

Gly Ser Ala Asp Gly Pro His Tyr Arg Ile Pro Ser Ala Pro Ala Arg
385                 390                 395                 400

Asp Ala Lys Ala His Ser Leu Ser Arg Glu Ala Ala Arg Asn Leu Arg
                405                 410                 415

Glu Arg Ser Lys Lys Phe Cys Lys Pro Pro Leu Ala Ser Pro Ala Arg
            420                 425                 430

Gly Gly Ser Ala Ser Pro Ser Met Arg Thr Leu Ser Pro Ala Ala Gln
        435                 440                 445

Lys Phe Val Arg Asn Ala Ile Ala Lys Ser Ser Ser Ser Val Asp Glu
    450                 455                 460

Thr Leu Arg Ala Ser Tyr Arg Gly Ser Thr Pro Ala Leu Ala Thr Pro
465                 470                 475                 480

Thr Arg Val Arg Ser Val Ser Arg Leu Gly Arg Asp Glu Ser Thr Val
                485                 490                 495

Ser Arg Ser Pro Ser Val Arg Asp Gly Ser Asn Pro Pro Trp
            500                 505                 510

<210> SEQ ID NO 19
<211> LENGTH: 19
<212> TYPE: DNA
<213> ORGANISM: Artificial Sequence
<220> FEATURE:
<223> OTHER INFORMATION: Polynucleotide

<400> SEQUENCE: 19
gaacctgcga ttggagtgt                                                   19

<210> SEQ ID NO 20
<211> LENGTH: 21
<212> TYPE: DNA
<213> ORGANISM: Artificial Sequence
<220> FEATURE:
<223> OTHER INFORMATION: Polynucleotide

<400> SEQUENCE: 20
caatcgagaa gatcatcgag c                                                21

<210> SEQ ID NO 21
<211> LENGTH: 21
<212> TYPE: DNA
<213> ORGANISM: Artificial Sequence
<220> FEATURE:
<223> OTHER INFORMATION: Polynucleotide

<400> SEQUENCE: 21
tggaatgtta tagtgcggtc c                                                21

<210> SEQ ID NO 22
<211> LENGTH: 21
<212> TYPE: DNA
<213> ORGANISM: Artificial Sequence
<220> FEATURE:
<223> OTHER INFORMATION: Polynucleotide

<400> SEQUENCE: 22
cggatgagag ttctcgatga g                                                21
```

```
<210> SEQ ID NO 23
<211> LENGTH: 19
<212> TYPE: DNA
<213> ORGANISM: Artificial Sequence
<220> FEATURE:
<223> OTHER INFORMATION: Polynucleotide

<400> SEQUENCE: 23
attttgccga tttcggaac                                               19

<210> SEQ ID NO 24
<211> LENGTH: 20
<212> TYPE: DNA
<213> ORGANISM: Artificial Sequence
<220> FEATURE:
<223> OTHER INFORMATION: Polynucleotide

<400> SEQUENCE: 24
catctgatca gccaccgagt                                              20

<210> SEQ ID NO 25
<211> LENGTH: 20
<212> TYPE: DNA
<213> ORGANISM: Artificial Sequence
<220> FEATURE:
<223> OTHER INFORMATION: Polynucleotide

<400> SEQUENCE: 25
ctcagttaaa ggcgcctcac                                              20

<210> SEQ ID NO 26
<211> LENGTH: 20
<212> TYPE: DNA
<213> ORGANISM: Artificial Sequence
<220> FEATURE:
<223> OTHER INFORMATION: Polynucleotide

<400> SEQUENCE: 26
catctgatca gccaccgagt                                              20

<210> SEQ ID NO 27
<211> LENGTH: 20
<212> TYPE: DNA
<213> ORGANISM: Artificial Sequence
<220> FEATURE:
<223> OTHER INFORMATION: Polynucleotide

<400> SEQUENCE: 27
ctcagttaaa ggcgcctcac                                              20

<210> SEQ ID NO 28
<211> LENGTH: 19
<212> TYPE: DNA
<213> ORGANISM: Artificial Sequence
<220> FEATURE:
<223> OTHER INFORMATION: Polynucleotide

<400> SEQUENCE: 28
gcggagagtg acggagaat                                               19

<210> SEQ ID NO 29
<211> LENGTH: 20
<212> TYPE: DNA
<213> ORGANISM: Artificial Sequence
<220> FEATURE:
<223> OTHER INFORMATION: Polynucleotide
```

```
<400> SEQUENCE: 29
cccggtctgt gtacttgctg                                              20
```